United States Patent
Retailleau et al.

(10) Patent No.: US 12,137,880 B2
(45) Date of Patent: Nov. 12, 2024

(54) CLEANING DEVICES FOR INSTRUMENTS, AND RELATED METHODS

(71) Applicant: INTUITIVE SURGICAL OPERATIONS, INC., Sunnyvale, CA (US)

(72) Inventors: Sascha Retailleau, San Francisco, CA (US); Robert C. Reid, Fairfield, CT (US); Eoin Brennan, Branford, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 896 days.

(21) Appl. No.: 17/150,417

(22) Filed: Jan. 15, 2021

(65) Prior Publication Data

US 2021/0219832 A1   Jul. 22, 2021

Related U.S. Application Data

(60) Provisional application No. 63/045,922, filed on Jun. 30, 2020, provisional application No. 62/961,745, filed on Jan. 16, 2020.

(51) Int. Cl.
*A61B 1/00* (2006.01)
*A61B 1/05* (2006.01)
*A61B 1/12* (2006.01)

(52) U.S. Cl.
CPC .......... *A61B 1/126* (2013.01); *A61B 1/00128* (2013.01); *A61B 1/00135* (2013.01); *A61B 1/05* (2013.01)

(58) Field of Classification Search
CPC ................ A61B 1/126; A61B 1/00128; A61B 1/00135; A61B 1/05; A61B 1/00142
See application file for complete search history.

(56) References Cited

U.S. PATENT DOCUMENTS 5,695,448 A * 12/1997 Kimura ................ A61B 1/0005
600/125
8,852,208 B2   10/2014 Gomez et al.
(Continued)

FOREIGN PATENT DOCUMENTS

WO    WO-2020081963 A1    4/2020

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Timothy J Neal
(74) *Attorney, Agent, or Firm* — JONES ROBB, PLLC

(57) ABSTRACT

In accordance with at least one embodiment of the present disclosure, a system includes an imaging instrument with a shaft including a proximal end, a distal end, and a lens at a distal end portion of the shaft. The system also includes a collar at a proximal end portion of the shaft. A cleaning device coupled to the imaging instrument includes a tubular member sized to receive the shaft of the imaging instrument. The cleaning device also includes a latching element coupled to the tubular member and configured to couple to the collar to retain the tubular member on the shaft of the imaging instrument and maintain a relative rotational relationship between the tubular member and the shaft of the imaging instrument. Devices and methods relate to cleaning devices for imaging instruments.

22 Claims, 20 Drawing Sheets

(56) References Cited

U.S. PATENT DOCUMENTS

| | | |
|---|---|---|
| 9,295,524 B2 | 3/2016 | Schena et al. |
| 9,358,074 B2 | 6/2016 | Schena et al. |
| 2006/0293559 A1* | 12/2006 | Grice ..................... A61B 1/122 |
| | | 600/102 |
| 2009/0247827 A1* | 10/2009 | Secrest ................ A61B 1/0014 |
| | | 600/131 |

* cited by examiner

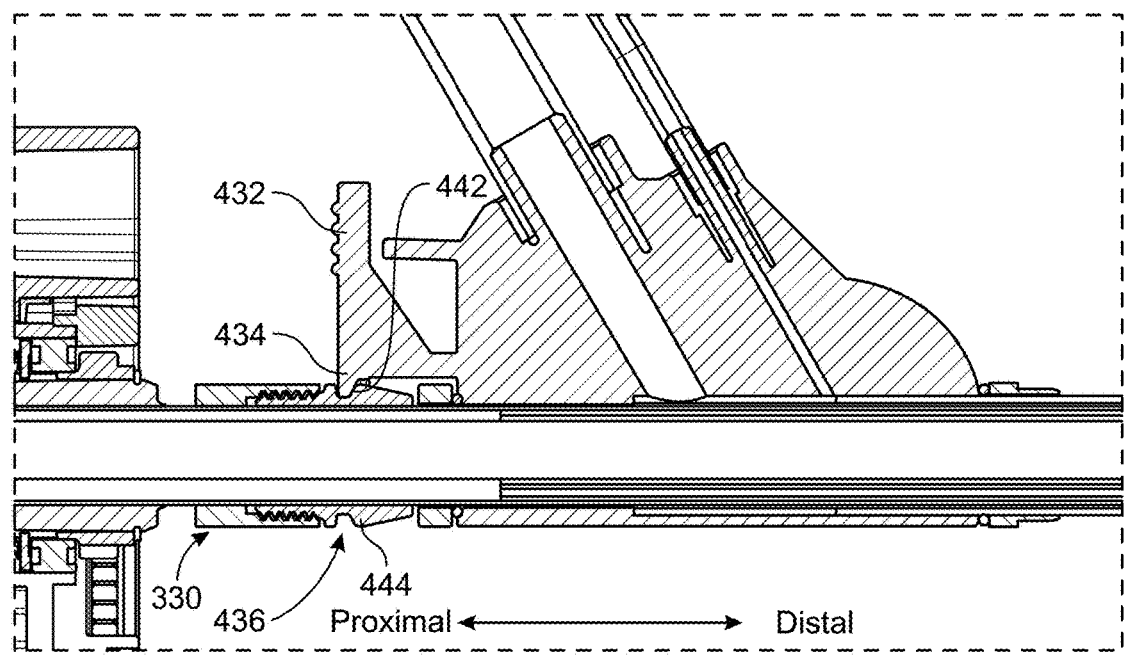
FIG. 5
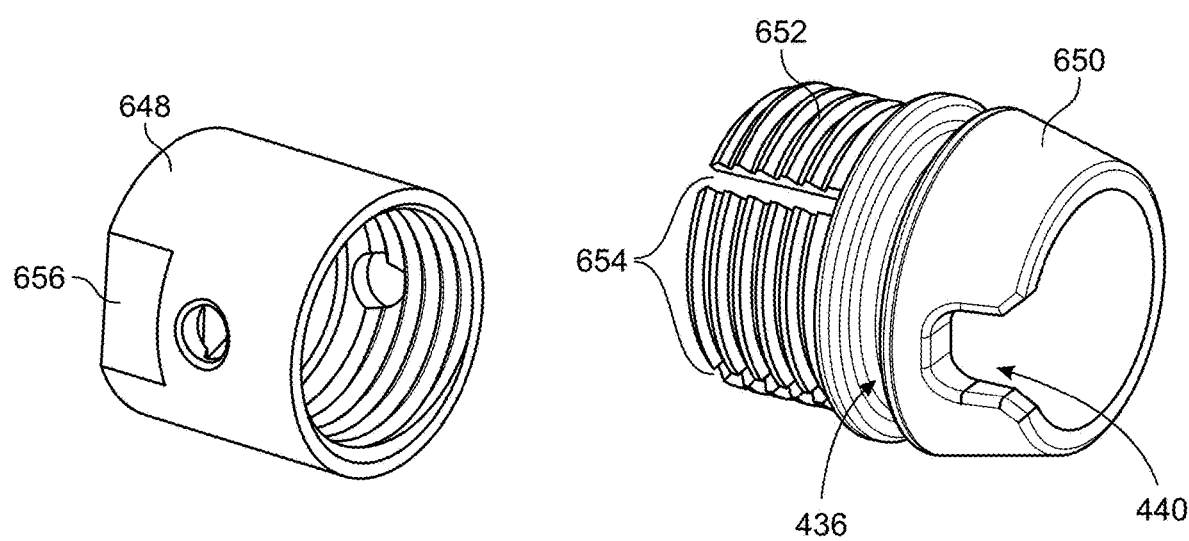
FIG. 6
FIG. 7

CLEANING DEVICES FOR INSTRUMENTS, AND RELATED METHODS

CROSS-REFERENCE TO RELATED APPLICATIONS

This application claims priority to U.S. Provisional Application No. 63/045,922 (filed Jun. 30, 2020) titled CLEANING DEVICES FOR IMAGING INSTRUMENTS, DEVICES, AND METHODS, and U.S. Provisional Application No. 62/961,745 (filed Jan. 16, 2020) titled CLEANING DEVICES FOR INSTRUMENTS, AND RELATED METHODS, the entire contents of each of which are incorporated by reference herein.

TECHNICAL FIELD

Aspects of the present disclosure relate to cleaning devices for instruments, such as medical or industrial instruments. For example, aspects of the present disclosure relate to imaging instruments including, but not limited to, for example, endoscopes and instruments with distal end cameras or other imaging or sensing devices used in remote surgical, diagnostic, therapeutic, and other treatment procedures.

INTRODUCTION

Imaging instruments, such as endoscopes, can be used to provide a view of a subject site of interest, such as a remote site where a surgical or other procedure is being performed. Images of the remote visual field taken by the imaging instrument can be transmitted to a display device (e.g., an electronic display) viewable by a user. One example of such a use for an imaging instrument is during minimally invasive surgical, diagnostic, therapeutic, sensing, and/or other treatment procedures (collectively referred to as "surgical procedures" herein), which can be carried out through manually actuated tools or tools actuated via computer-assisted teleoperated systems, such as robotic surgical systems. During such a procedure, there is a potential for a lens, viewport, or other viewing portion of the imaging instrument through which the remote site is imaged to become partly or fully occluded by tissue, fluids, or other materials. This can result in images of the remote site being partly or fully obscured. In some cases, the imaging instrument may be removed, cleaned, and reinserted to continue obtaining images of the subject site. But the process of removing, cleaning, and reinserting the imaging instrument can be time-consuming, which can impact the overall time of the surgical procedure.

A need exists for devices, and for related systems and methods, that facilitate clearing a viewing portion of an imaging instrument. For example, a need exists for devices, systems, and methods that enable cleaning a viewing portion of an imaging instrument while the instrument remains in situ at a remote site. Further, a need exists to provide such devices that can be installed on existing endoscope designs, i.e., cleaning devices that can be retrofitted to endoscopes not originally equipped with such cleaning devices. And still further, a need exists to provide such devices with features that facilitate installation at the correct orientation on the imaging instrument so as to properly carry out the cleaning, as well as facilitating removal from the imaging instrument.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one embodiment of the present disclosure, a system includes an imaging instrument with a shaft including a proximal end, a distal end, and a lens at a distal end portion of the shaft. The system also includes a collar at a proximal end portion of the shaft. A cleaning device coupled to the imaging instrument includes a tubular member sized to receive the shaft of the imaging instrument. The cleaning device also includes a latching element coupled to the tubular member and configured to couple to the collar to retain the tubular member on the shaft of the imaging instrument and maintain a relative rotational relationship between the tubular member and the shaft of the imaging instrument.

In accordance with at least another embodiment of the present disclosure, a cleaning device for an imaging instrument includes a tubular member sized to receive a shaft of an imaging instrument, a collar including a retention feature, a collar latching element movably coupled to the tubular member, and a tubular member anti-rotation feature. The tubular member anti-rotation feature is configured to fix a relative rotational orientation between the tubular member and the collar.

In accordance with yet another embodiment of the present disclosure, a system comprises an instrument and a tubular member. The instrument comprises a shaft, and the shaft comprises an engagement portion. The engagement portion comprises one or more lead-in shoulders, a proximal apex area of the one or more lead-in shoulders, and a recess at the proximal apex area. The tubular member comprises a registration tab configured to be received in the recess of the engagement portion in the predetermined rotational orientation relative to the shaft. Contact between the registration tab and the one or more lead-in shoulders as the tubular member is moved in a proximal direction along the shaft rotationally aligns the tubular member in the predetermined rotational orientation relative to the shaft.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

FIG. 5 is a side cross-sectional view of the portion of the imaging instrument and cleaning device of FIGS. 2 and 3.

FIG. 6 is a perspective view of a first piece of a two-piece collar according to an exemplary embodiment of the present disclosure.

FIG. 7 is a perspective view of a second piece of the two-piece collar according to the embodiment of FIG. 6.

DETAILED DESCRIPTION

Figure 1:
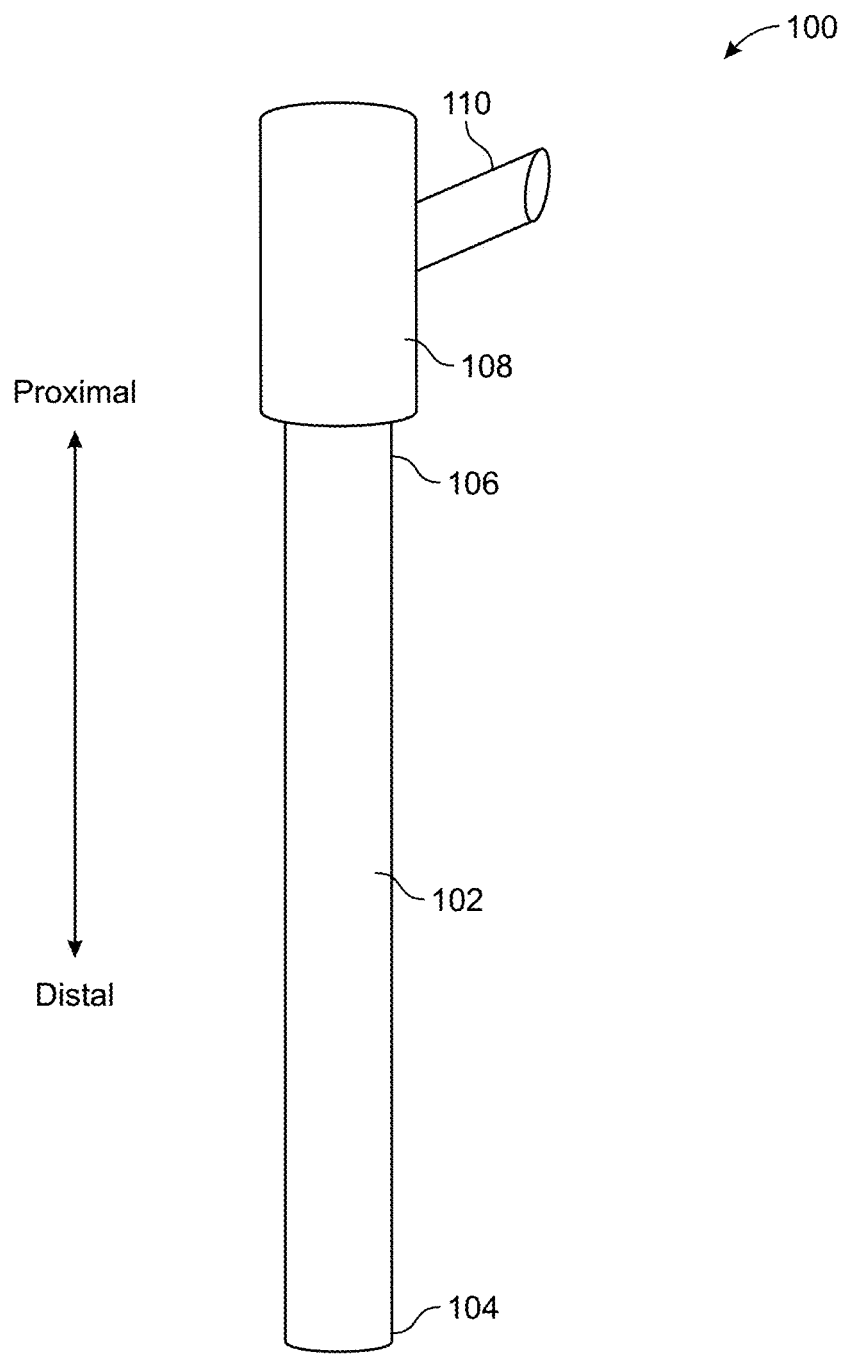
FIG. 1 is a schematic side view of an embodiment of a cleaning device for cleaning an imaging instrument according to the present disclosure.

The present disclosure provides various embodiments of cleaning devices that can be used for cleaning of an imaging instrument (such as, for example, an endoscope) in situ, for example, while the instrument is at a location to image a remote site, such as during a remote surgical procedure or other remote procedure, for example. In various exemplary device, such cleaning devices can optionally be configured to be installed on imaging instruments not originally equipped with cleaning devices. In other words, cleaning devices according to various embodiments can be configured to be retrofit to imaging instruments not otherwise designed for use with such cleaning devices. For example, in some embodiments, the cleaning devices can be configured to couple with an imaging instrument by a retention collar that is permanently or removably installed on a shaft of the imaging instrument.

A retention collar can include various features that interface with the shaft of an imaging instrument to maintain the collar in a specified position on the shaft. Due to interaction between the cleaning device and the viewing portion (e.g., lens, aperture, etc.) of the imaging instrument, the axial location and orientation of the cleaning device relative to the imaging instrument can affect the cleaning efficacy of the cleaning device and thus the imaging performance of the imaging instrument. Accordingly, the collar, or other components of the imaging instrument to which the cleaning device can be coupled for retention on the imaging instrument shaft, can include features that maintain an axial position and a rotational orientation of the cleaning device with respect to the imaging instrument shaft.

The cleaning device can optionally be configured to promote ease of installation to, and removal from, the imaging instrument. Such configurations can facilitate rapid transferal of the imaging instrument from one location to another during a surgical procedure by enabling a user to place multiple cleaning device in separate locations, such as positioning the cleaning devices at desired locations through incisions and/or ports positioned in a patient's body. An imaging instrument can then be transferred between cleaning devices as desired by the user. When used in this manner, the cleaning devices can be analogous to a cannula that facilitates both advancement of an imaging instrument to a subject site and also includes functionality for clearing debris and contamination from the viewing portion (e.g., lens, aperture, etc.) of the imaging instrument.

Cleaning devices of the present disclosure can include functionality similar to that described in International Patent App. Pub. No. WO2020/081963 (filed Oct. 18, 2019) titled CLEANING DEVICES FOR IMAGING INSTRUMENTS, DEVICES, AND METHODS, the entire contents of which are incorporated by reference herein. For example, in some embodiments, cleaning devices of the present disclosure can include a manifold that includes one or more fluid inlets for connection to one or more fluid sources. The manifold can be rotatably coupled with a tubular member that extends to, or slightly beyond, a distal end portion of the imaging instrument. The tubular member can include one or more fluid passageways that fluidically couple the manifold to one or more nozzles at a distal end of the tubular member. The nozzles can be configured to direct a flow of fluid across the viewing portion (e.g., lens) of the imaging instrument to clear the imaging instrument, as discussed in greater detail in International Patent App. Pub. No. WO2020/081963, incorporated by reference above.

While the exemplary embodiments discussed herein relate primarily to cleaning devices for imaging instruments such as endoscopes, various aspects and features of devices according to the present disclosure can be used on other instruments, such as other medical or industrial tools. Such aspects can include various attachment features, self-aligning features, and other features described in detail below.

Referring now to FIG. 1, a schematic view of a cleaning device according to an embodiment of the present disclosure is shown. In the embodiment of FIG. 1, the cleaning device 100 includes a tubular member 102 having a distal end 104 and a proximal end 106. The tubular member is dimensioned to fit around a shaft of an imaging instrument, such as imaging instrument 212 shown in FIG. 2. The proximal end 106 of the tubular member 102 is coupled to and rotatable relative to a manifold portion 108 that receives a proximal end portion of the shaft of the imaging instrument. The manifold portion 108 comprises one or more fluid inlets 110 configured to be fluidically coupled with one or more supplies of cleaning fluid (e.g., a liquid or gas) (not shown). One or more fluid outlets at the distal end 104 of the tubular member 102 are fluidically coupled to the fluid inlets 110 by one or more fluid passages (also not shown). In some embodiments, the fluid passages are defined at least partially by the shaft of the imaging instrument and by the tubular member 102 when the shaft of the imaging instrument is received within the tubular member 102. In other words, the fluid passages can be defined between the shaft and the tubular member 102. The fluid passages can optionally be integrated with the tubular member 102, such as being formed partially or completely within the wall of the tubular member 102. The one or more fluid outlets are positioned such that when the imaging instrument shaft is within the tubular member 102, the one or more fluid outlets are positioned proximate a distal viewing portion of the imaging instrument. Fluid flowing into the one or more fluid inlets 110 is directed through the one or more fluid passages and from the one or more fluid outlets to clear material from the viewing portion of the imaging instrument.

Figure 2:
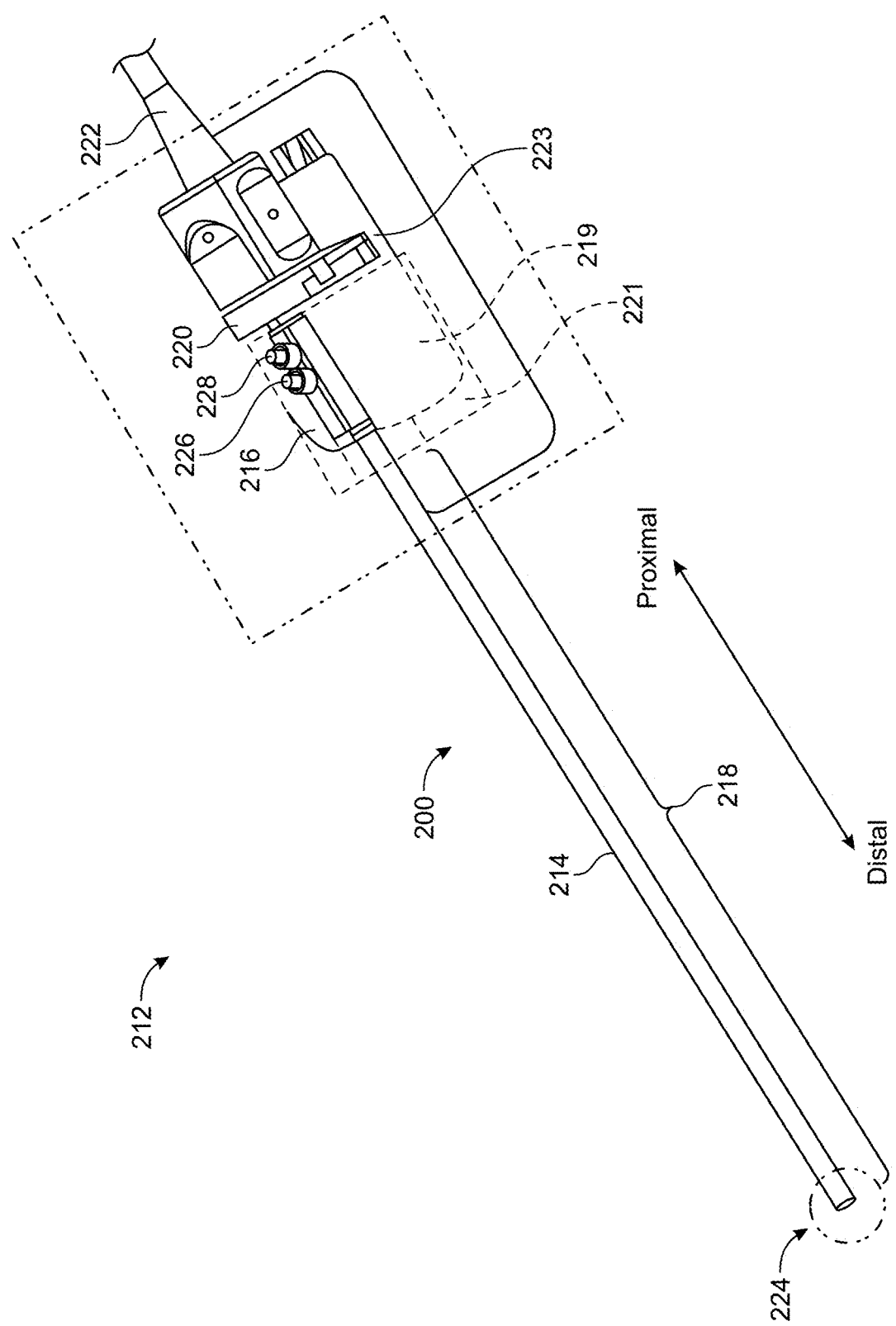
FIG. 2 is a perspective view of an embodiment of an imaging instrument and cleaning device operably coupled to the imaging instrument according to the present disclosure.

Referring now to FIG. 2, an embodiment of a cleaning device is shown installed on an imaging instrument. The cleaning device 200 includes a tubular member 214 that covers the imaging instrument shaft 218, as described with reference to FIG. 1. A manifold 216 of the cleaning device 200 is positioned around a proximal end portion of the imaging instrument shaft 218 and includes fluid inlets 226 and 228. The imaging instrument shaft 218 includes a distal end portion 224, at which a distal viewing portion 225 such as a lens, window, or other imaging aperture is located.

Figure 19:
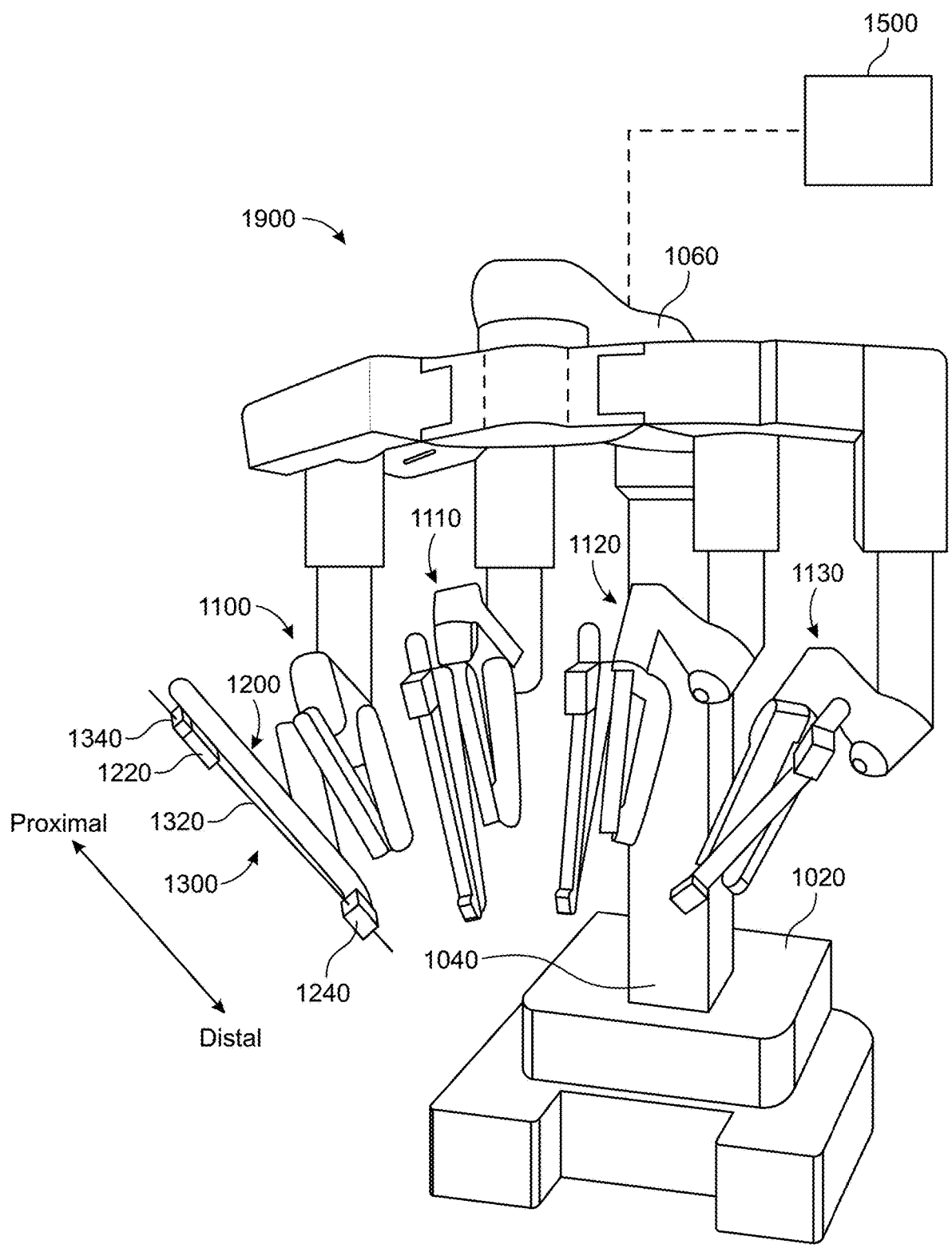
FIG. 19 is a perspective view of a manipulating system according to an exemplary embodiment of the present disclosure.
Figure 20:
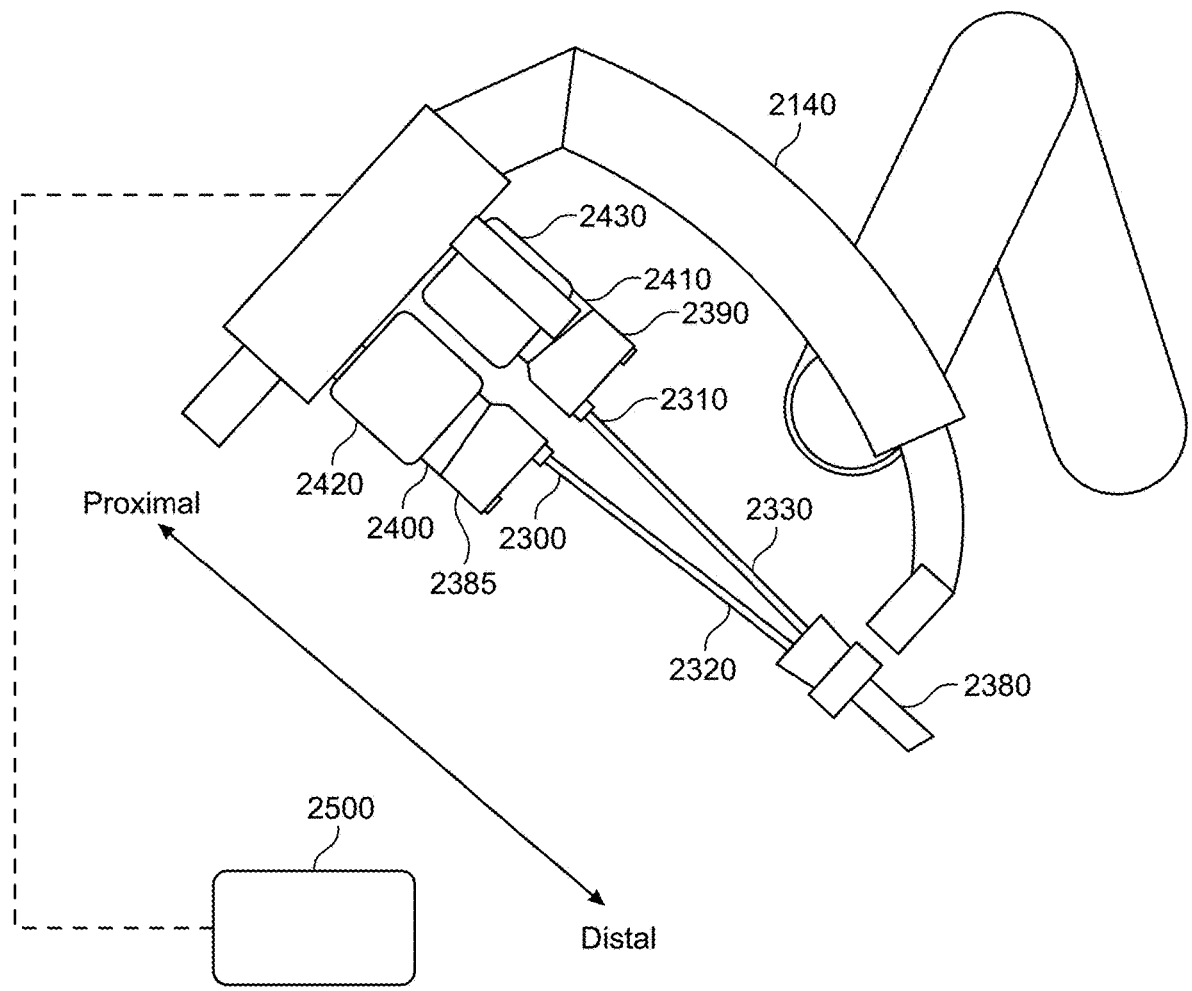
FIG. 20 is a partial schematic view of an embodiment of a manipulator arm of a manipulating system according to the present disclosure with two instruments in an installed position.

The imaging instrument 212 can be operably coupled to a manipulator, such as manipulator arms 1100, 1110, 1120, or 1130 of system 1900 (FIG. 19) or manipulator arm 2140 in FIG. 20. A connector portion 220 of the imaging instrument 212 is configured to couple with the instrument carriage 219 through a sterile instrument adaptor 223, and the connector portion 220 can optionally include various controls and connection components (such as a wire bundle 222) for connection to other portions of a surgical system (not shown) such as manipulator controls or other input devices, display devices, power supplies, or other components. Alternatively, the imaging instrument can be configured for manual (e.g., handheld) use.

The cleaning device 200 extends from the connector portion 220 of the imaging instrument 212 to the distal end portion 224 of the shaft 218. The manifold 216 is positioned proximate the instrument carriage 219 when the imaging instrument 212 is coupled to the instrument carriage 219, and the tubular member 214 extends from the manifold 216 to the distal end portion 224 of the instrument shaft 218. The manifold 216 includes one or more fluid inlet ports 226, 228 (two being shown in FIG. 2) that are each configured to accept a flow of a cleaning fluid, such as saline solution, carbon dioxide, or other fluids. The one or more fluid inlet ports 226, 228 can optionally be configured to attach to hoses or other fluid supply tubes of a surgical system (such as manipulating system 1900 shown in FIG. 19) or supporting components of such a system. In an embodiment, the one or more fluid inlet ports 226, 228 are configured with Luer-type fittings (not shown); however, various other types of fluid connectors, or a direct attachment, also may be utilized.

The cleaning device 200 is configured to direct fluid introduced at the one or more fluid inlet ports 226, 228 to the distal end portion 224 of the shaft 218 (shown in dashed lines). In various embodiments, the manifold 216 and tubular member 214 comprise one or more fluid passages extending between the one or more fluid inlet ports 226, 228 to one or more nozzles (not shown) located at a distal end of the tubular member 214 proximate the distal end portion 224 of the shaft 218. In use, fluid travels from the one or more fluid inlet ports 226, 228, through the one or more passages in the manifold portion 216 and the tubular member 214 and exits the one or more nozzles. Flow of fluid from the nozzle(s) is directed toward (e.g., across) the distal viewing portion of the imaging instrument, thus washing away bodily fluids, tissue, or other debris from the distal viewing portion and removing the debris from the distal viewing portion of the imaging instrument, as discussed in greater detail in International Patent App. Pub. No. WO2020/081963, incorporated by reference above.

As discussed above, cleaning devices, such as cleaning device 200, can include various features and components that facilitate use of the cleaning device on imaging instruments not originally equipped with a cleaning device or otherwise configured to accept such a cleaning device. For example, a collar or other component that can be removably or permanently coupled to a shaft of an imaging instrument can be used to retain a cleaning device on an instrument shaft and to position the cleaning device in a desired rotational and axial relationship to the imaging instrument.

Figure 3:
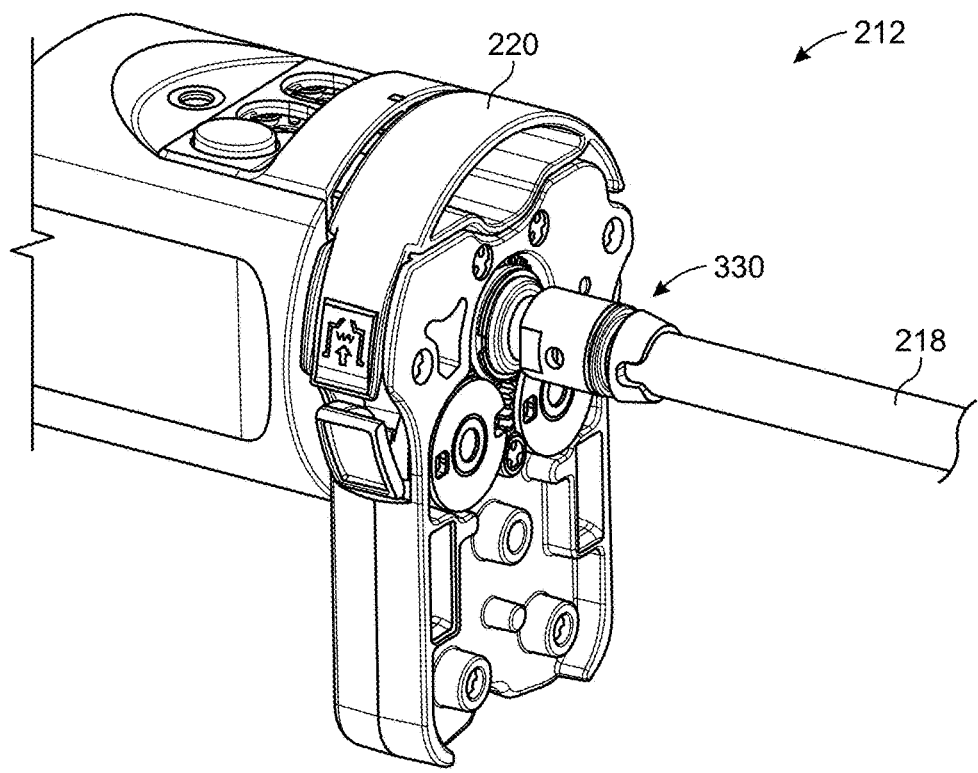
FIG. 3 is an enlarged perspective view of a portion of the imaging instrument of FIG. 2 with various components omitted to show the imaging instrument shaft and a collar according to an exemplary embodiment of the present disclosure.

Referring now to FIG. 3, an enlarged perspective view of the imaging instrument 212 is shown, with the cleaning device 200 omitted to show the shaft 218 of the imaging instrument 212. An embodiment of a collar 330 also is shown. The collar 330 is coupled to the shaft 218 adjacent the connector portion 220. The collar 330 includes one or more retention features that couple the collar 330 to the shaft 218 in a manner that prevents axial or rotational movement of the collar 330 relative to the shaft 218, as discussed further in connection with FIG. 4. As noted above, maintaining axial positioning and rotational orientation of the cleaning device 200 relative to the shaft 218 can ensure that the cleaning device 200 functions properly and does not unduly obscure the viewing portion (e.g., lens) of the imaging instrument 212.

The collar 330 can include various features to enable a secure installation of the collar 330 in a fixed axial position and rotational orientation over a shaft of an imaging instrument that does not include any coupling features, e.g., a straight, smooth portion of shaft 218 of the imaging instrument 212. FIGS. 6 and 7 show detailed views of the collar 330 of FIG. 3. The collar 330 comprises two separate components engageable with one another. The two separate components can include an internally threaded sleeve 648 and a collet 650. The collet 650 includes features configured for coupling with the cleaning device 200, such as a groove 436 on its outer surface and a recess 440 at its distal end. The collet 650 also comprises an externally threaded shank 652 proximal to the groove 436. The collet 650 can include features that facilitate the collet gripping the shaft 218. For example, the threaded shank 652 includes longitudinal reliefs 654 that permit some degree of flexibility of portions of the shank 652 separated by the reliefs 654, thereby enabling the portions of the shank 652 to tighten around the shaft 218 as the threaded sleeve 648 is tightened over the collet 650, as discussed further below.

To install the collar 330 over the instrument shaft 218, first the sleeve 648 is placed over the shaft 218 (FIG. 3) and moved proximally of the desired location of the collar 330. The collet 650 is placed over the shaft 218 and advanced proximally to the desired location. Once the collet 650 is placed in the desired location on the shaft 218, i.e., in the desired axial position and rotational orientation as discussed above, the sleeve 648 is threaded over the shank 652 of the collet 650 and tightened, e.g., via wrench flats 656 on the sleeve 648. The sleeve 648 can include an internal taper such that as the sleeve 648 is tightened over the shank 652 of the collet 650, the portions of the shank 652 tighten around the shaft 218 and securely hold the collet 650 in place.

Because the location of the collar 330 determines the axial position and rotational orientation of the cleaning device 200 relative to the shaft 218, as explained below with respect to FIGS. 4 and 5, correct positioning of the collar 330 can be important to ensure that the cleaning device 200 and imaging instrument 212 both function in a desirable manner. In some embodiments of the disclosure, a separate fixture, such as a jig, could be used to hold the collar 330 in the desired location on the shaft 218.

Figure 4:
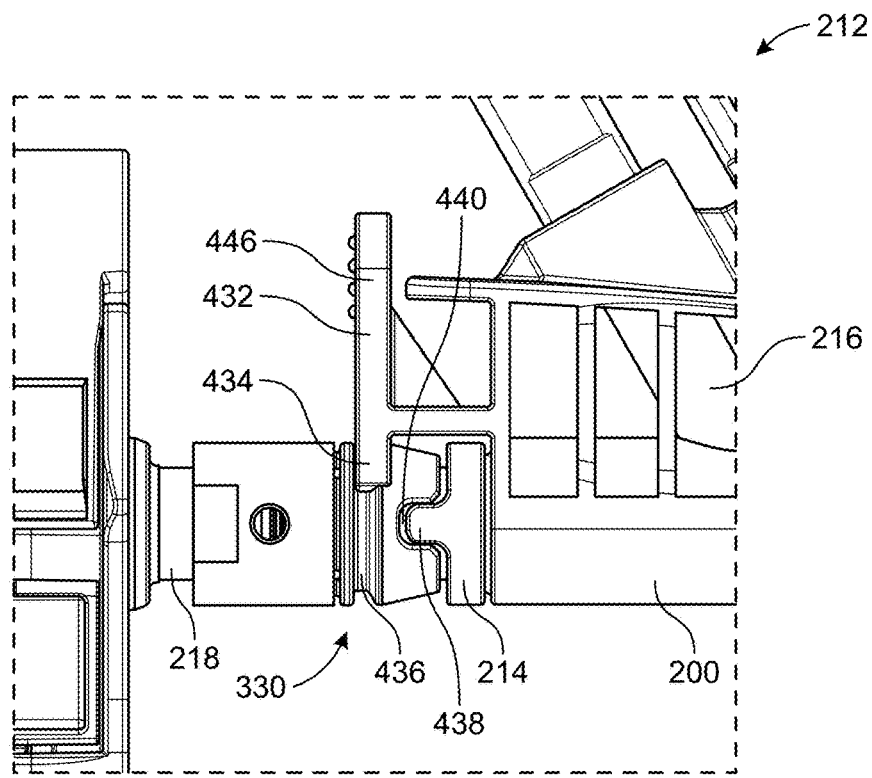
FIG. 4 is an enlarged, detailed side view of the imaging instrument and cleaning device of FIGS. 2 and 3.

Referring now to FIG. 4, a side view of the imaging instrument 212 of FIG. 3 with the cleaning device attached to the collar 330 discussed in connection with FIGS. 6-7 is shown. The cleaning device 200 includes a manifold 216 and a tubular member 214. As further discussed in detail in International Patent App. Pub. No. WO2020/081963, incorporated above, the manifold 216 can optionally be rotatable relative to the tubular member 214. Permitting rotation of the manifold 216 relative to the tubular member 214 enables rotation (i.e., roll) of the shaft 218 for an imaging instrument having such a rotatable shaft. Allowing such rotation of the shaft 218 can, for example, facilitate obtaining the desired view or image of a subject site with the imaging instrument 212. Because the manifold 216 is rotatable relative to the shaft 218, such rotation of the shaft 218 does not result in twisting or tangling of any fluid sources (e.g., hoses or other conduits) connected to the fluid inlet ports 226, 228 (FIG. 2).

The cleaning device 200 includes features configured to interact with the collar 330 to retain the cleaning device 200 in position on the shaft 218 of the imaging instrument 212. For example, in the embodiment of FIG. 4, the manifold 216 has a latching element 432 with a flange 434 sized and shaped to interact with a groove 436 in the collar 330 to hold the cleaning device 200 in place over the shaft 218. The groove 436 can optionally extend circumferentially around the collar 330. In this embodiment, with the latching element 432 coupled to the manifold 216, such a groove can enable full rotation of the shaft 218 and collar 330. That is, the flange 434 is free to rotate within the groove 436, thereby enabling rotation of the shaft 218 while permitting the manifold 216 to remain stationary. The latching element 432 has a lever portion 446 to facilitate removal of the cleaning device 200 from the imaging instrument 212, as discussed below.

The cleaning device 200 and collar 330 can include an anti-rotation mechanism that orients the tubular member 214 relative to the shaft 218 and maintains a set rotational orientation between the tubular member 214 and the shaft 218 when the cleaning device 200 is secured to the collar 330. The anti-rotation mechanism can include a first anti-rotation feature on the tubular member 214 and a second anti-rotation feature on the collar 330. For example, in the embodiment of FIG. 4, the first anti-rotation feature is a registration tab 438 on the tubular member 214 that mates with a second anti-rotation feature in the form of a recess 440 on the collar 330. Mechanical interaction between the registration tab 438 and the recess 440 prevents relative rotation between the tubular member 214 and the collar 330. Thus, when the collar 330 is installed on the shaft 218, the anti-rotation mechanism prevents relative rotation between the tubular member 214 and the shaft 218 and maintains the desired rotational orientation of the tubular member 214 relative to the shaft 218.

In some embodiments, to ensure proper functioning of the cleaning device 200 and the imaging instrument 212, the tubular member 214 of the cleaning device 200 must be seated against the distal end 224 (FIG. 2) of the shaft 218 of the imaging instrument 212 in the axial (i.e., longitudinal) direction. Accordingly, in some exemplary embodiments of the present disclosure, the cleaning device 200 can be configured to preload the tubular member 214 against the shaft 218. For example, referring now to FIG. 5, which shows a view like FIG. 4 but in cross-section, the flange 434 of the latching element 432 features a ramped distal face 442. The groove 436 features a corresponding ramped proximal surface 444. The ramped proximal surface 444 and ramped distal face 442 mechanically interact to provide a longitudinal preload force holding the tubular member 214 of the cleaning device 200 against the distal end 224 of the shaft 218.

To install the cleaning device 200 over the shaft 218, the shaft 218 is inserted into a proximal end of the tubular member 214, and the manifold is aligned as needed with other components of the imaging instrument 212, such as the connector portion 220. Once the latching element 432 reaches the collar 330 of the shaft 218, the registration tab 438 and the recess 440 are aligned, allowing the registration tab 438 to be received in the recess 440 and the flange 434 to enter the groove 436. In this configuration, i.e., as shown in FIGS. 4 and 5, the cleaning device 200 is retained on the imaging instrument and the assembly is ready for use.

To remove the cleaning device 200 from the imaging instrument 212, the lever portion 446 of the latching element 432 is depressed to remove the flange 434 from the groove 436 of the collar 330. Once the flange 434 is uncoupled from the collar 330, to the shaft 218 can be withdrawn from the cleaning device 200 tubular member 214 and the cleaning device 200 removed from the imaging instrument 212.

In some exemplary embodiments of the disclosure, the collar and/or cleaning device can include features that enable the cleaning device to be secured to the collar in more than one position, so that the cleaning device can be properly installed even if the collar is not in a single, predetermined position.

Figure 8:
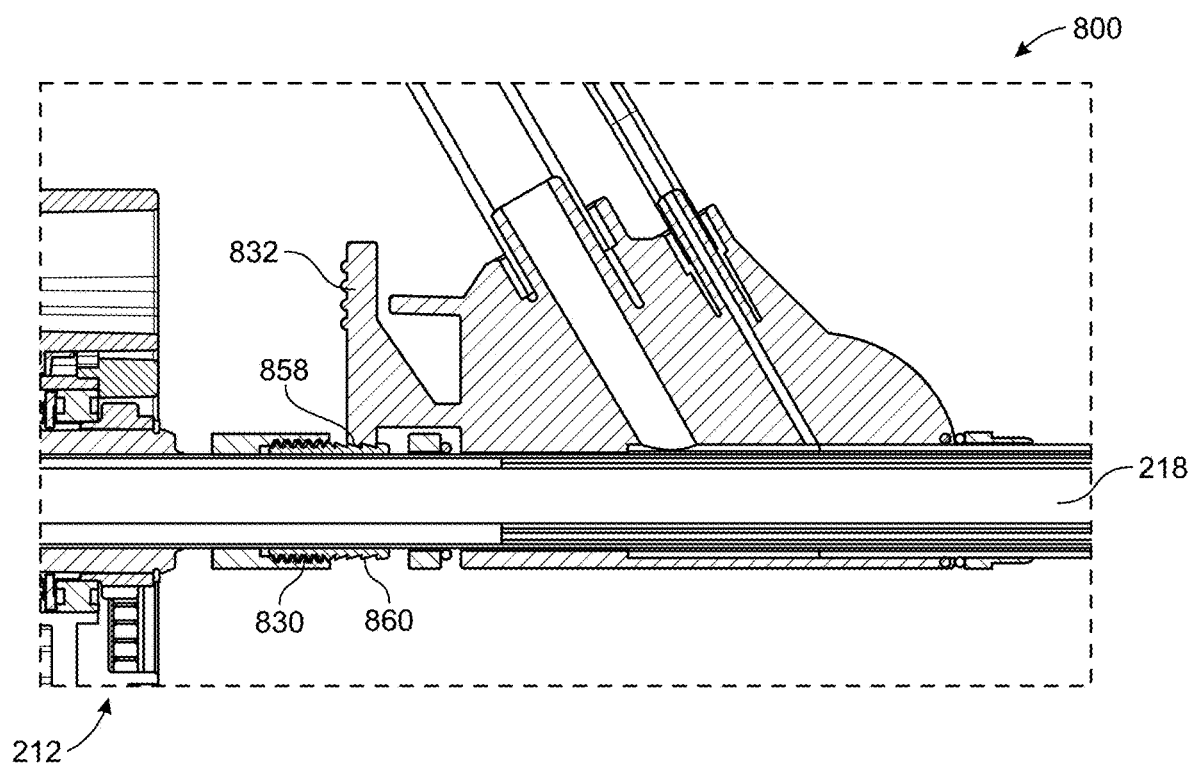
FIG. 8 is a side cross-sectional view of an imaging instrument and cleaning device according to another embodiment of the present disclosure.

For example, FIG. 8 shows another exemplary embodiment of a cleaning device 800 and imaging instrument 212 according to the present disclosure. In the embodiment of FIG. 8, a latching element 832 of the cleaning device 800 includes one or more barbs 858 at an end of a flange 834 that engage corresponding barbs 860 on the circumference of a collar 830. Each of the latching element 832 and the collar 830 can optionally include multiple barbs. As the cleaning device 800 is installed over the imaging instrument 212, the barbs 858 and 860 engage one another via a ratcheting action. The cleaning device 800 can be advanced over the imaging instrument 212 until the cleaning device 800 is seated against the distal end 224 of the shaft 218 of the imaging instrument 212. Engagement between the barbs 858 and 860 holds the cleaning device 800 in place on the imaging instrument 212. The configuration of the cleaning device 800 ensures that the cleaning device 800 can be seated tightly against the distal end 224 of the shaft 218, even if the axial position of the collar 830 relative to the distal end 224 of the shaft 218 varies due to, for example, shaft length variations due to manufacturing tolerance and/or variations in axial location of the collar 830. Provision of multiple barbs on one or both of the cleaning device 800 and the collar can enable correct positioning of the cleaning device 800 over the imaging instrument 212 even if the collar 830 is not in a precisely defined axial position. That is, one of the potential advantages of the embodiment of FIG. 8 is that the axial position of the collar 830 along a shaft of the imaging instrument can potentially have a relatively larger tolerance, because the cleaning device 800 can be coupled to the collar 830 in multiple axial positions.

Figure 9:
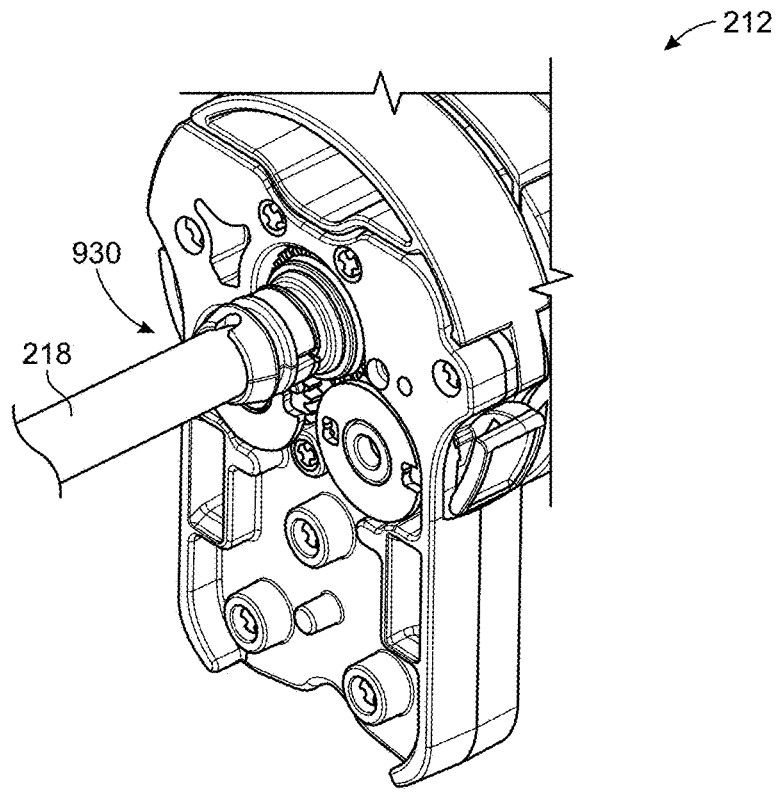
FIG. 9 is a perspective view similar to the view of FIG. 3 of a portion of an imaging instrument according to another exemplary embodiment of the present disclosure.
Figure 10:
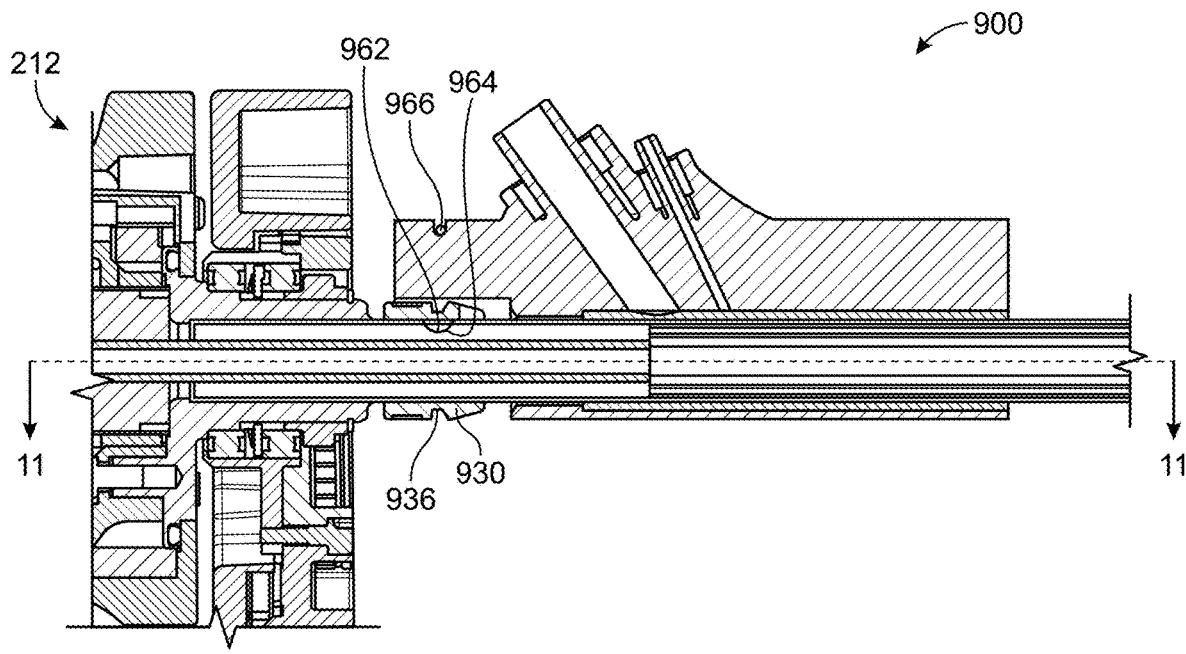
FIG. 10 is a side cross-sectional view of an imaging instrument and cleaning device according to another exemplary embodiment of the present disclosure.
Figure 11:
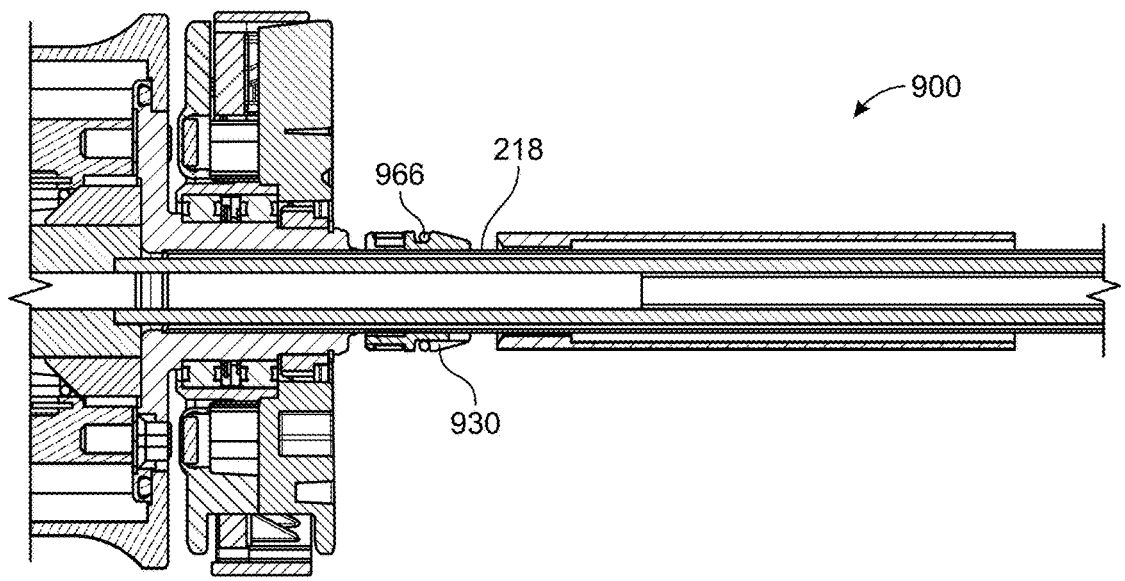
FIG. 11 is a cross-sectional view along section 11-11 of the imaging instrument of FIG. 10.
Figure 12:
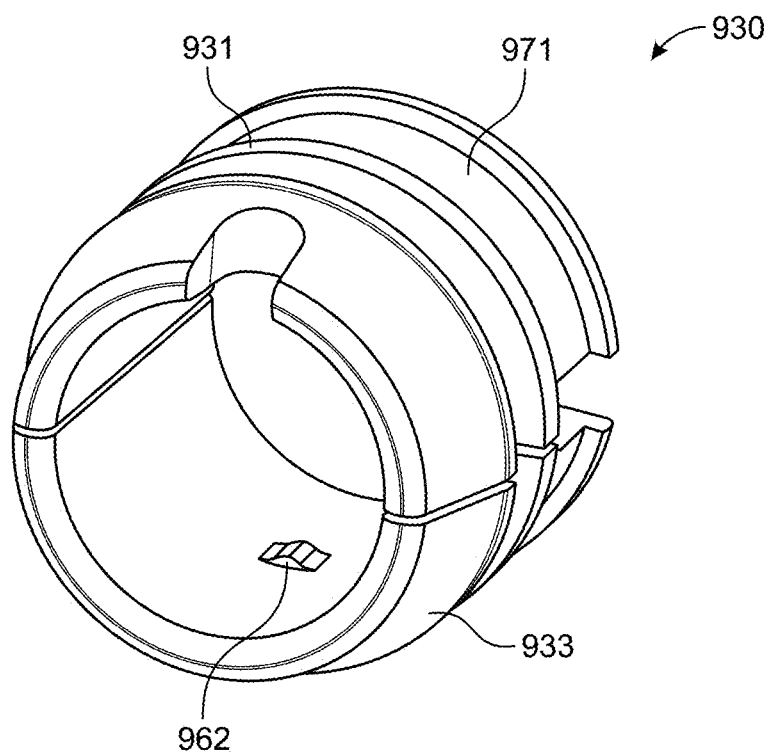
FIG. 12 is a perspective view of a collar according to another embodiment of the present disclosure.
Figure 13:
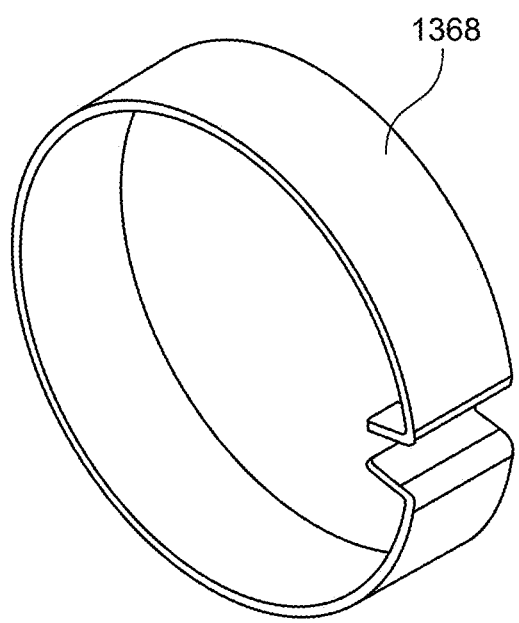
FIG. 13 is a perspective view of a collar retainer clip according to an embodiment of the present disclosure.

Referring now to FIGS. 9-13, another exemplary embodiment of a cleaning device 900 and imaging instrument 912 according to the present disclosure is shown. FIG. 9 shows a backend portion of the imaging instrument 912 with a collar 930 installed on a shaft 918. FIG. 10 shows a side cross-sectional view of the cleaning device 900 and imaging instrument 912. In this embodiment, the collar 930 includes at least one registration protrusion 962 on an interior surface of the collar 930. The registration protrusion is received within a dimple 964 provided in the shaft 218. The collar 930 includes a groove 936 extending circumferentially around the collar 930, similar to groove 436 in embodiment of FIGS. 3-7. Alternatively, the collar 930 can include barbs 860 similar to those discussed in connection with FIG. 8. The cleaning device 900 includes a spring clip 966 (illustrated in FIGS. 10 and 11) that engages the groove 936 when the cleaning device 900 is installed over the shaft 918.

The dimple 964 can be formed in an existing shaft, e.g., a shaft of an endoscope not specifically configured for a cleaning device. For example, the dimple 964 can optionally be formed in the shaft of an existing imaging instrument as part of an installation procedure. The dimple can be formed with a tool such as a punch, a drift, or other tool. The position of the dimple 964 can be set by tooling such as a jig to ensure the dimple 964 is placed in a desired axial position and rotational orientation for correct operation of the cleaning device 900, as discussed above. Alternatively, the dimple 964 can be formed as part of a manufacturing process of the shaft 918.

In the embodiment of FIGS. 9-13, the collar 930 comprises two portions 931, 933 (FIG. 12), each forming a circumferential portion of the collar 930. To install the collar 930 over the shaft 218 of the imaging instrument 212, the two portions 931, 933 are positioned around the shaft 218. The collar 930 includes a retainer groove 971 into which a retainer band 968 (FIGS. 9 and 13) is installed. The retainer band 968 retains the two portions 931, 933 over the shaft 918, and the interface between the registration protrusion 962 and the dimple 964 ensures the collar 930 is located and retained in a desired and fixed axial position and rotational orientation relative to the shaft 918. The retainer band 968 can comprise an elastic material such as steel or other metal alloys, polymers, composite materials, or other materials. The retainer band 968 can be configured to apply a constant compressive retaining force against the retainer groove 971 to maintain the collar 930 in position on the shaft 218.

Figure 14:
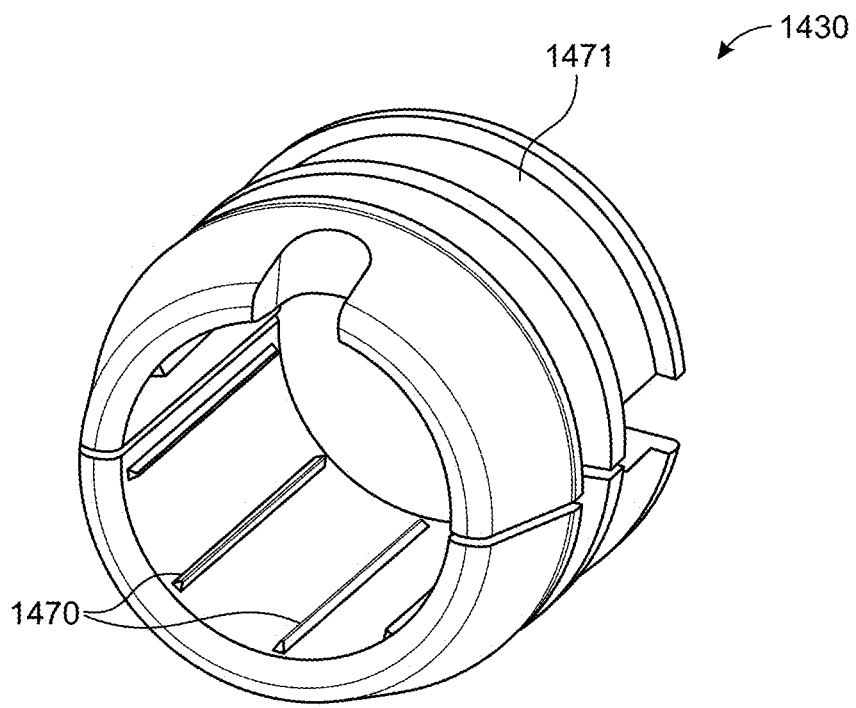
FIG. 14 is a perspective view of a collar according to another exemplary embodiment of the present disclosure.

Features other than the registration protrusion 962 and dimple 964 can be used to retain a collar in position on a shaft of an imaging instrument. For example, referring now to FIG. 14, another exemplary embodiment of a collar 1430 is shown. The collar 1430 is similar to the collar 930 of the embodiment of FIGS. 9-13, but the collar 1430 features a plurality of longitudinal ridges 1470 on an interior surface of the collar 1430. The collar 1430 can be installed on an imaging instrument shaft by pressing the two collar portions around the shaft until the longitudinal ridges 1470 engage the shaft. In an exemplary embodiment, slight surface deformation of the outer surface of the shaft may occur. A retainer, such as retainer band 968 of FIGS. 9 and 13 can then be installed over the collar 1430 (e.g., in retainer groove 1471) to retain the collar 1430 on the shaft. The longitudinal ridges 1470 assist in maintaining the installed axial position and rotational orientation of the collar 1430.

Figure 15:
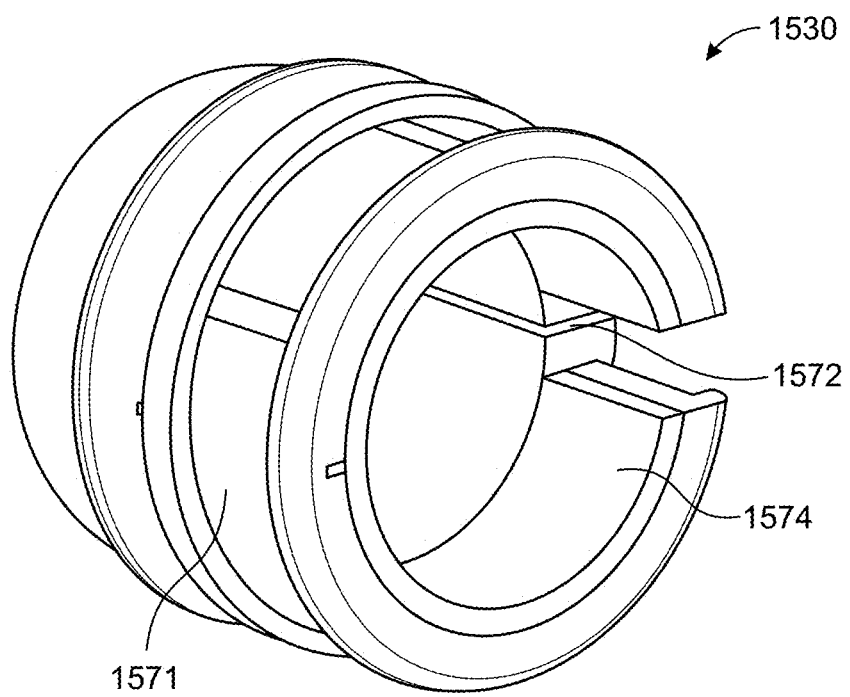
FIG. 15 is a perspective view of a collar according to another embodiment of the present disclosure.

Referring now to FIG. 15, another exemplary embodiment of a collar 1530 is shown. In this exemplary embodiment, the collar 1530 includes a split feature 1572 along a single side. The collar 1530 includes a gripping portion 1574 made of a material configured to grip the imaging instrument shaft and inhibit or prevent movement of the collar 1530 relative to the shaft. In an exemplary embodiment, the gripping portion 1574 can comprise a polymer material, such as, for example, silicone rubber or other material chosen to provide relatively high friction with the shaft.

To install the collar 1530, a tool such a wedge (not shown) can be inserted in the split feature 1572 to widen the interior diameter of the collar 1530 enough to enable the collar 1530 to easily slide over the imaging instrument shaft. Once the collar 1530 is located correctly, the wedge can be removed and a retainer, such as the retainer band 968 (FIG. 13) placed in a retainer groove 1571. Pressure from the retainer band 968 and friction of the gripping portion 1574 on the shaft retains the collar 1530 in the desired location.

Figure 16:
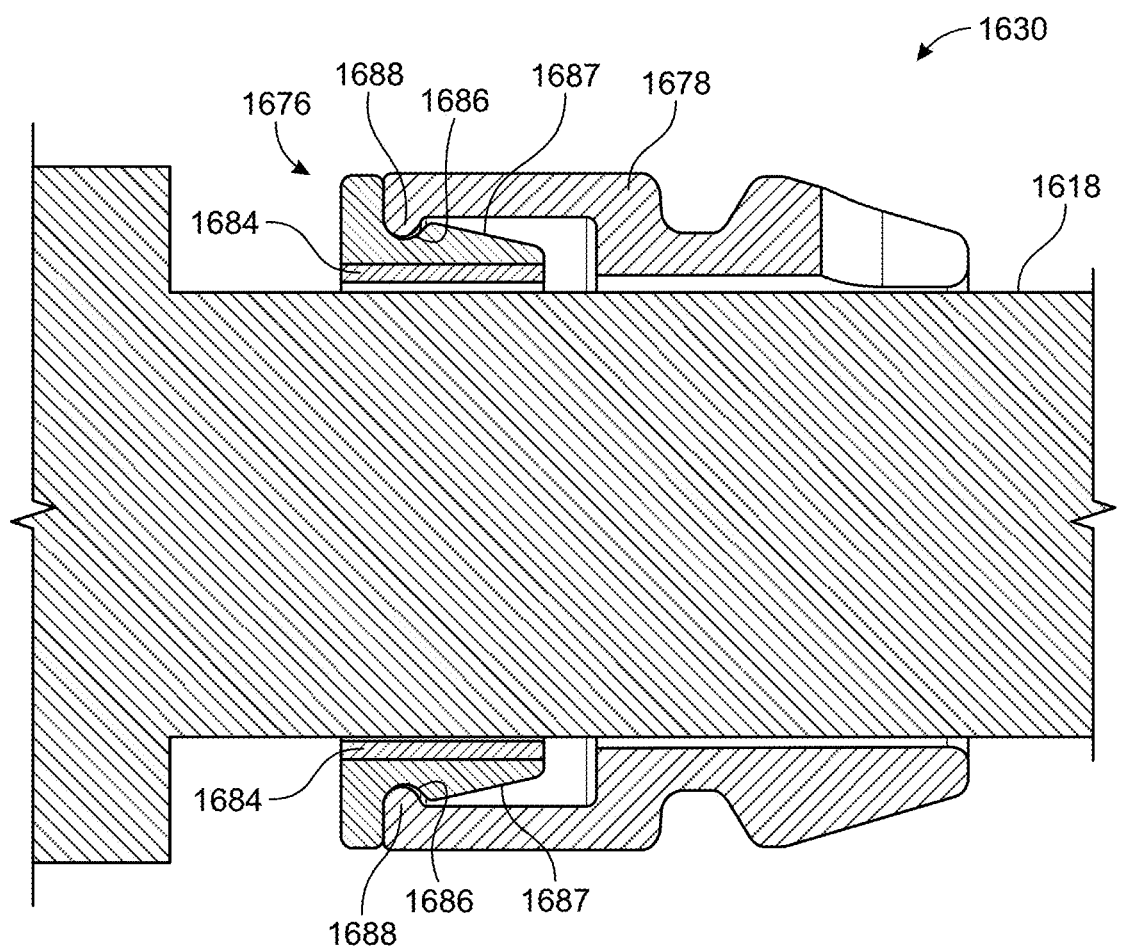
FIG. 16 is a side cross-sectional schematic view of a collar fit on a shaft of an imaging instrument according another exemplary embodiment of the present disclosure.

FIG. 16 shows a side, schematic cross-sectional view of another embodiment of a collar according to the present disclosure. In this embodiment, a collar 1630 comprises a collet 1676 and a retaining sleeve 1678 having features similar to any of the embodiments discussed herein. The collet 1676 has an interior portion 1684 comprising a resilient material. The collet 1676 comprises one or more recesses 1686 on an exterior portion of the collet 1676 and a ramped portion 1687 proximal to the one or more recesses 1686. The retaining sleeve 1678 comprises an annular shape and includes one or more protruding retention members 1688. To install the collar 1630, the collet 1676 is placed at the desired position on the shaft 1618. The retaining sleeve 1678 is then advanced over the collet 1676, and the retention members 1688 bear against the ramped portion 1687, causing the resilient material of the interior portion 1684 to grip the shaft. The retaining sleeve 1678 is advanced over the collet 1676 until the one or more protruding retention members 1688 engage the one or more recesses 1686, and the retaining sleeve 1678 maintains pressure on the collet 1676 to keep the collet 1676 in place on the shaft 1618. To enable the retaining sleeve 1678 to compress the collet 1676 tightly onto the shaft 1618, the collet 1676 can be split in two halves, like the collar 1430 of FIG. 14, or can have a single split feature, like the split feature 1572 of the collar 1530 of FIG. 15, or can have other arrangements that facilitate compression of the collet 1676 around the shaft 1618.

Figure 17:
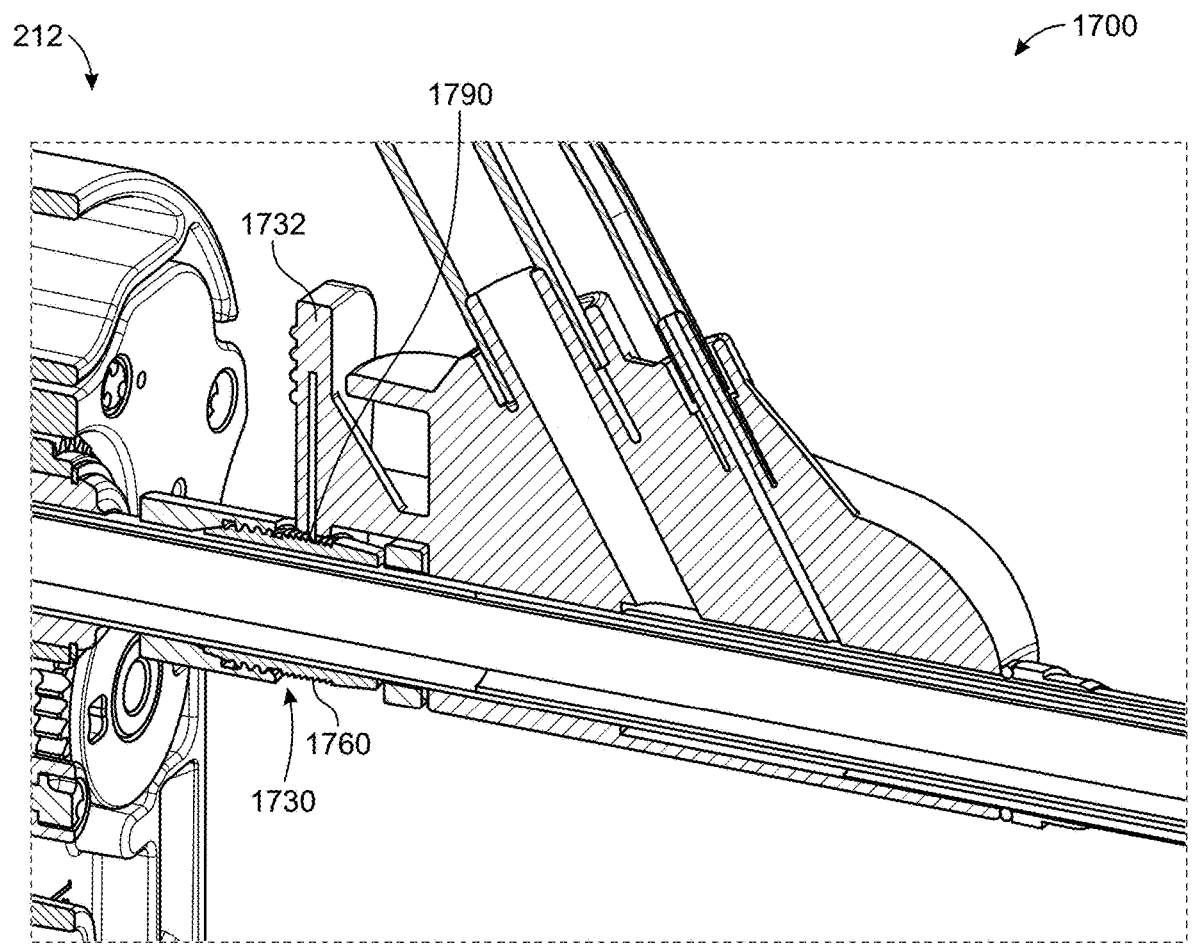
FIG. 17 is a side cross-sectional view of an imaging instrument and cleaning device according to another exemplary embodiment of the present disclosure.

Referring now to FIG. 17, another exemplary embodiment of a cleaning device 1700 attached to an imaging instrument 212 is shown. The cleaning device 1700 is similar to cleaning device 800 of FIG. 8 in that the cleaning device 1700 includes a similar arrangement of a collar 1730 with barbs 1760 that engage with a latching element 1732 to retain the cleaning device 800 over a shaft 218 of the imaging instrument 212. In the embodiment of FIG. 17, the latching element 1732 includes a tooth 1790 that is at least partially embedded in the latching element 1732. The tooth 1790 can comprise a material harder than the material of the latching element 1732. For example, the latching element 1732 can comprise a polymer material to impart resilience and flexibility to the latching element 1732, and the tooth 1790 can comprise a harder, more durable material than the latching element 1732, such as, for example, a metal alloy or other material. The tooth 1790 can be configured to engage with the barbs 1760 on the collar 1730 to retain the cleaning device 1700 over the shaft 218.

Because the tooth 1790 comprises a relatively hard material, it can exhibit more wear resistance than the material of the latching element 1732. In some embodiments, the tooth 1790 can exhibit material characteristics similar to those of the collar 1730. Due to the greater hardness and associated wear resistance of the material of the tooth 1790, the tooth 1790 can be provided with a relatively small point of engagement with the collar 1730 and the barbs 1760 on the collar 1730 can be provided with a correspondingly fine pitch. Such an arrangement can provide a relatively fine degree of accuracy of axial positioning of the cleaning device 1700 over the shaft 218.

Figure 18:
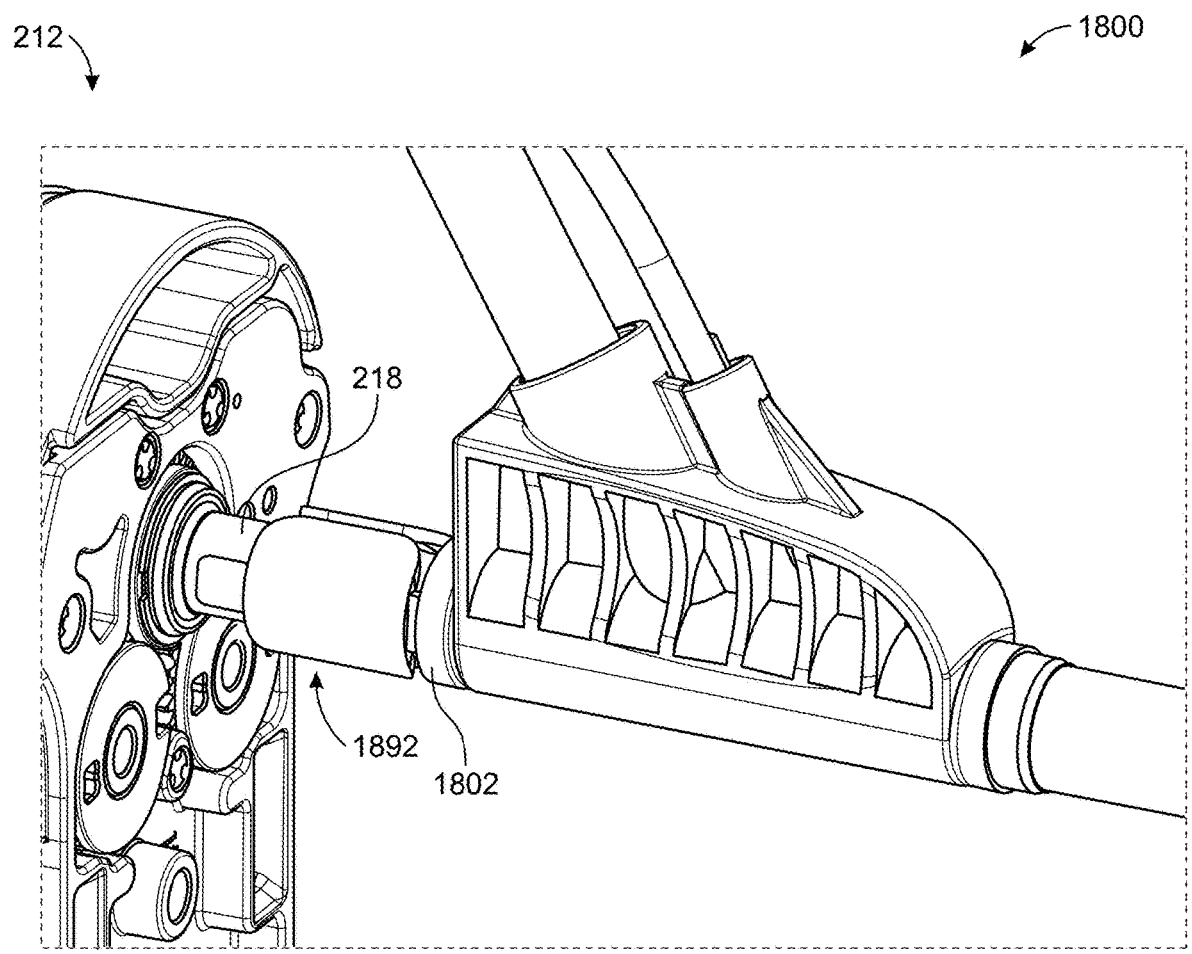
FIG. 18 is a perspective view of an imaging instrument and cleaning device according to yet another exemplary embodiment of the present disclosure.

Some cleaning devices according to the present disclosure can include a collar that is coupled to the cleaning device, and the collar and cleaning device are attached to the instrument shaft of an imaging device together as an assembly. For example, referring now to FIG. 18, an embodiment of a cleaning device 1800 is shown coupled to a shaft 218 of an imaging instrument 212. The cleaning device 1800 includes a collar 1892 that is coupled to a component of the cleaning device 1800, such as to a tubular member 1802. The collar 1892 includes movable features that can be engaged with the shaft 218. For example, in the embodiment of FIG. 18, two clamshell portions 1894 at least partially surround the shaft 218. The clamshell portions 1894 can be hinged relative to the shaft 218. To install the cleaning device 1800 on the shaft 218, the clamshell portions 1894 can be swung generally away from the shaft 218 as the cleaning device 1800 is advanced over the shaft 218. Once the cleaning device 1800 is installed over the shaft 218 and appropriately positioned and oriented relative to the shaft 218, the two clamshell portions 1894 can then be attached to the tubular member 1802. For example, the clamshell portions 1894 can be affixed to the tubular member 1802 by adhesive elements, such as two-sided adhesive tape previously affixed to an interior surface of each of the clamshell portions 1894.

Additionally or alternatively, the cleaning device 1800 can be affixed to the shaft 218 by a collar or other component attached to the tubular member 1802 or the manifold 1816, such as camming lock mechanisms that rely on friction fit or other types of clamps, bands, or other fasteners.

Cleaning devices according to the present disclosure optionally include various features that facilitate installation and removal of the cleaning device from the instrument shaft in an intuitive manner. Such features optionally also facilitate correct rotational alignment and axial latching of the cleaning device. While these features are shown generally herein in connection with cleaning devices for imaging instruments, such features are optionally included on devices other than cleaning devices, such as protective sheaths or other tubular members used with imaging devices, or other surgical or non-surgical (such as industrial) instruments, as discussed in connection with FIGS. 29 and 30.

Figure 21:
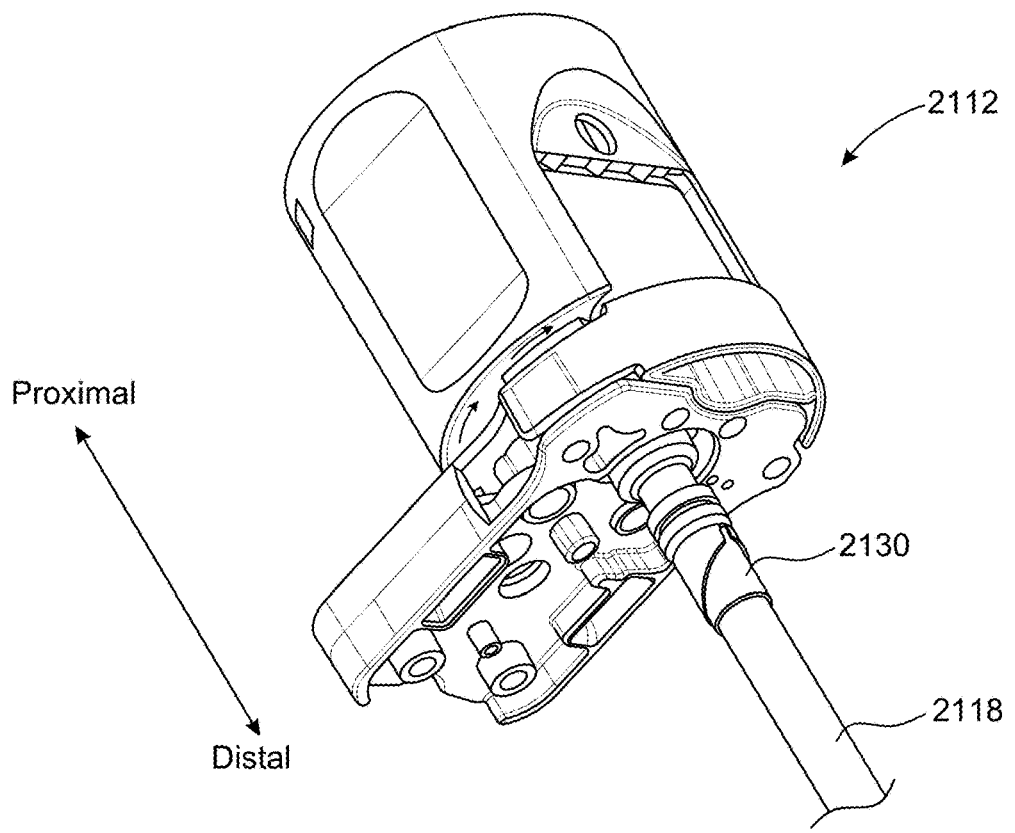
FIG. 21 is a perspective view of an imaging instrument with a collar according to an exemplary embodiment of present disclosure.

Referring now to FIG. 21, an exemplary embodiment of an imaging device 2112 is shown. The imaging device 2112 has a shaft 2118 and a collar 2130 positioned on a shaft 2118. The collar 2102 includes features configured to interact with features of a cleaning device, or other tubular member, including features configured to rotationally align the cleaning device with the imaging device 2112. In particular, the collar 2130 includes a self-aligning feature that is configured to establish a rotational alignment of the cleaning device relative to the imaging device 2112 and collar 2130 as the cleaning device is installed on the imaging device 2112. In the device shown in FIG. 21, the self-aligning feature is in the form of lead-in shoulders 2132 and 2133 (FIG. 22) that extend radially outward from the collar 2130 and slope around the collar's perimeter and along a length of the collar 2130.

Figure 22:
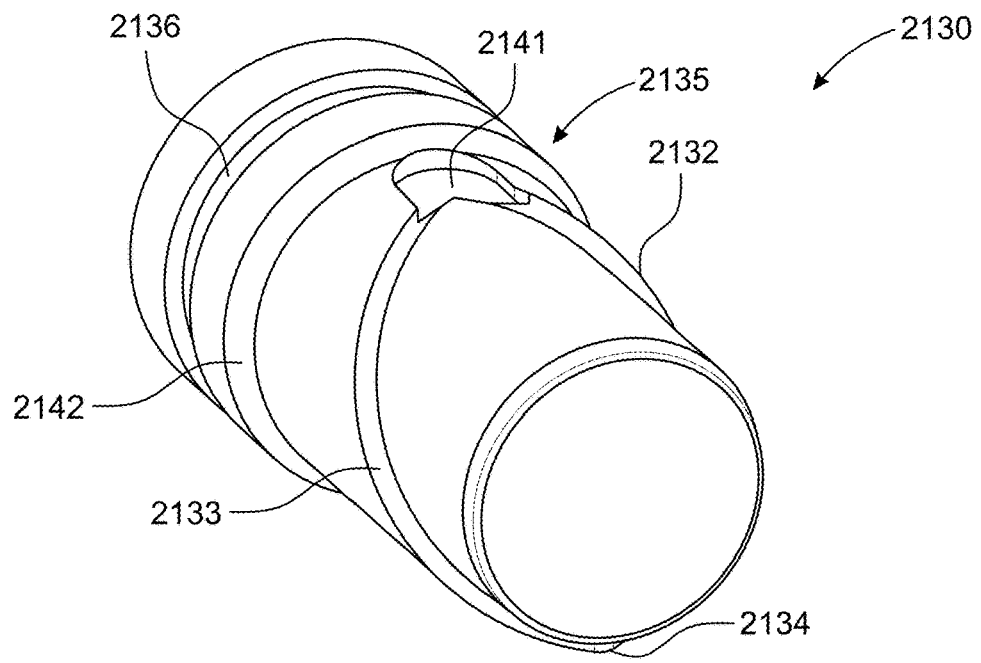
FIG. 22 is a perspective, detail view of the collar of FIG. 21.

FIG. 22 shows a detailed view of the collar 2130. The lead-in shoulders 2132 and 2133 extend generally in a partial spiral around the collar 2130, with each of the lead-in shoulders 2132 and 2133 sloping in opposite directions around the circumference of the collar 2130 from a distal base area 2134 to a proximal apex area 2135 at proximal ends of the lead-in shoulders 2132 and 2133. The lead-in shoulders may be alternatively described as being mirrored across a longitudinal bisecting plane of the collar 2130 so that they slope in a proximal direction away from the common distal base area 2134 and then towards the common proximal apex area 2135. The proximal apex area 2135 includes an optional recess 2141 configured to receive a registration tab 2138 (FIG. 23) of a cleaning device, as discussed in further detail in connection with FIG. 23.

The collar 2130 also optionally includes features configured to engage or otherwise mechanically interact with features of the cleaning device to retain the cleaning device on the collar 2130. For example, the collar 2130 includes a circumferentially extending groove 2136 located proximal to the recess 2141. A radially tapered region 2142 extends circumferentially around the collar 2130. The circumferentially extending groove 2136 accepts a retaining member, such as a retention pin or other device, as further discussed in connection with FIG. 23. The circumferentially extending groove 2136 is shown extending a full 360 degrees around the collar 2130 in embodiments herein to enable full rotation of the shaft 2118 by ensuring the collar 2130 and shaft 2118 can rotate about their longitudinal axes relative to the retaining member. However, the circumferentially extending groove 2136 can extend around less than 360 degrees around the collar 2130 depending on the amount of rotation desired for the shaft 2118, such as 180 degrees, 90 degrees, or fewer.

The collar 2130 can be fastened to the shaft of the imaging device 2112 by any appropriate process or device, such as, but not limited to, any of the approaches discussed herein in connection with collars 330, 830, 930, 1430, 1530, 1630, 1730, and 1892. In the device of FIGS. 21 and 22, the collar 2130 is permanently fastened to the shaft 2118 of the imaging device 2112 by a welding process, such as various inert gas welding processes, laser welding, or any other welding process.

Figure 23:
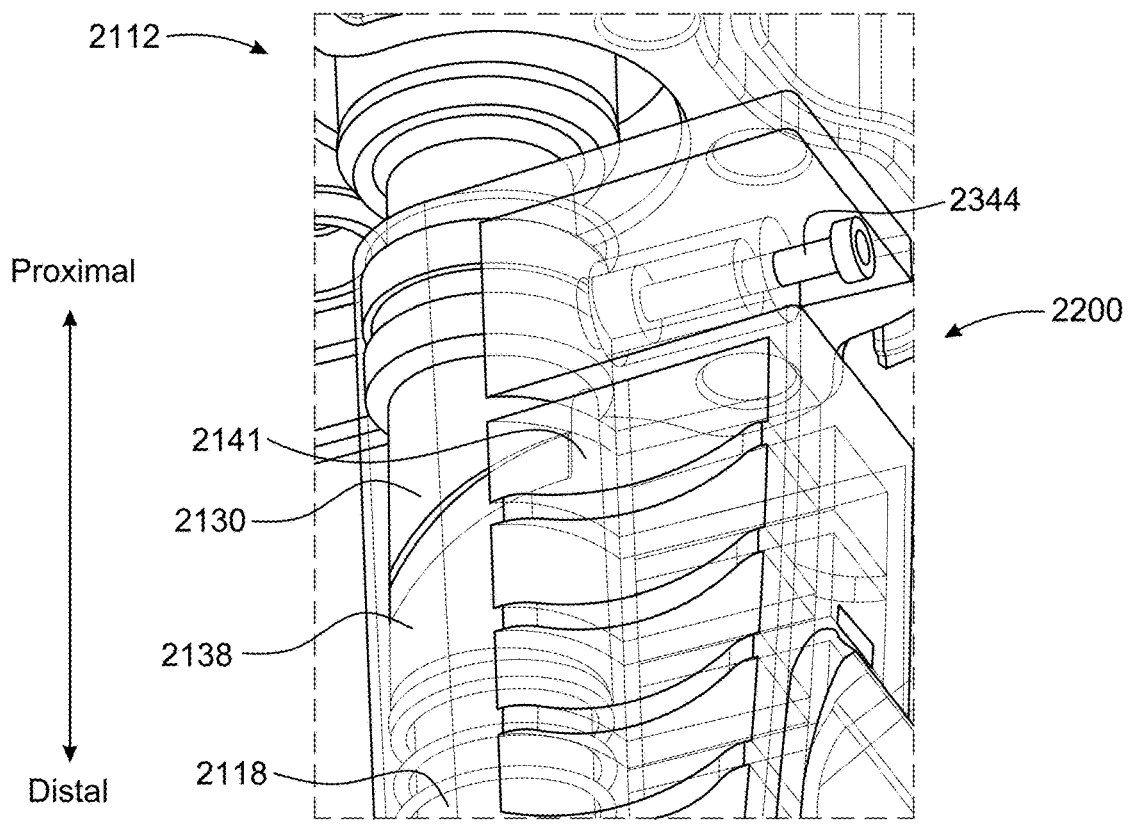
FIG. 23 is a perspective, detail view of the imaging instrument of FIG. 21 with a cleaning device according to an exemplary embodiment of the present disclosure.

Referring now to FIG. 23, a cleaning device 2200 is shown attached to the imaging device 2112. To facilitate illustration of the various features of the cleaning device 2200 and the manner in which they interact with features of the collar 2130, portions of the cleaning device 2200 are shown as hidden (dashed) lines. The cleaning device 2200 optionally includes features that, in conjunction with the features of the collar 2130, ensure rotational alignment, in a predetermined manner, between the cleaning device 2200 and the imaging device 2112.

The cleaning device 2200 optionally includes a registration tab 2138 that is received by the recess 2141 of the collar 2130. Engagement of the registration tab 2138 in the recess 2141 establishes and maintains a predetermined rotational orientation of the cleaning device 2200 with the collar 2130 and thus with the shaft 2118 of the imaging device 2112. The registration tab 2138 also interacts with the lead-in shoulders 2132 and 2133 (FIG. 22) of the collar 2130 to rotationally align the cleaning device 2200 with the shaft 2118 regardless of the initial orientation of the shaft 2118 relative to the cleaning device 2200 upon initial insertion of the shaft 2118 in the cleaning device 2200. For example, if a user inserts the shaft 2118 into the cleaning device 2200 with a relative rotational orientation at which the registration tab 2138 does not align with the recess 2141 of the collar 2130, as the cleaning device 2200 is pushed proximally over the shaft 2118, contact between the registration tab 2138 and either of the lead-in shoulders 2132 and 2133 causes rotation of the cleaning device 2200 relative to the shaft 2118 until the registration tab 2138 is aligned with and enters the recess 2141.

The cleaning device 2200 further includes a latching element configured to retain the cleaning device 2200 axially on the shaft 2118, such as, for example, any of the latching elements 432, 832, or 1732. In the exemplary embodiment of FIG. 23, the latching element comprises a retention pin 2344. The retention pin 2344 is optionally biased radially inwardly, e.g., by a spring or other biasing element. As the cleaning device 2200 is advanced over the shaft 2118 by a user, the retention pin 2344 contacts the radially tapered region 2142 and is forced radially outward as it rides up the radially tapered region 2142, until the retention pin 2344 drops radially inward into the circumferential groove 2136, thereby retaining the cleaning device 2200 on the shaft 2118.

Figure 24:
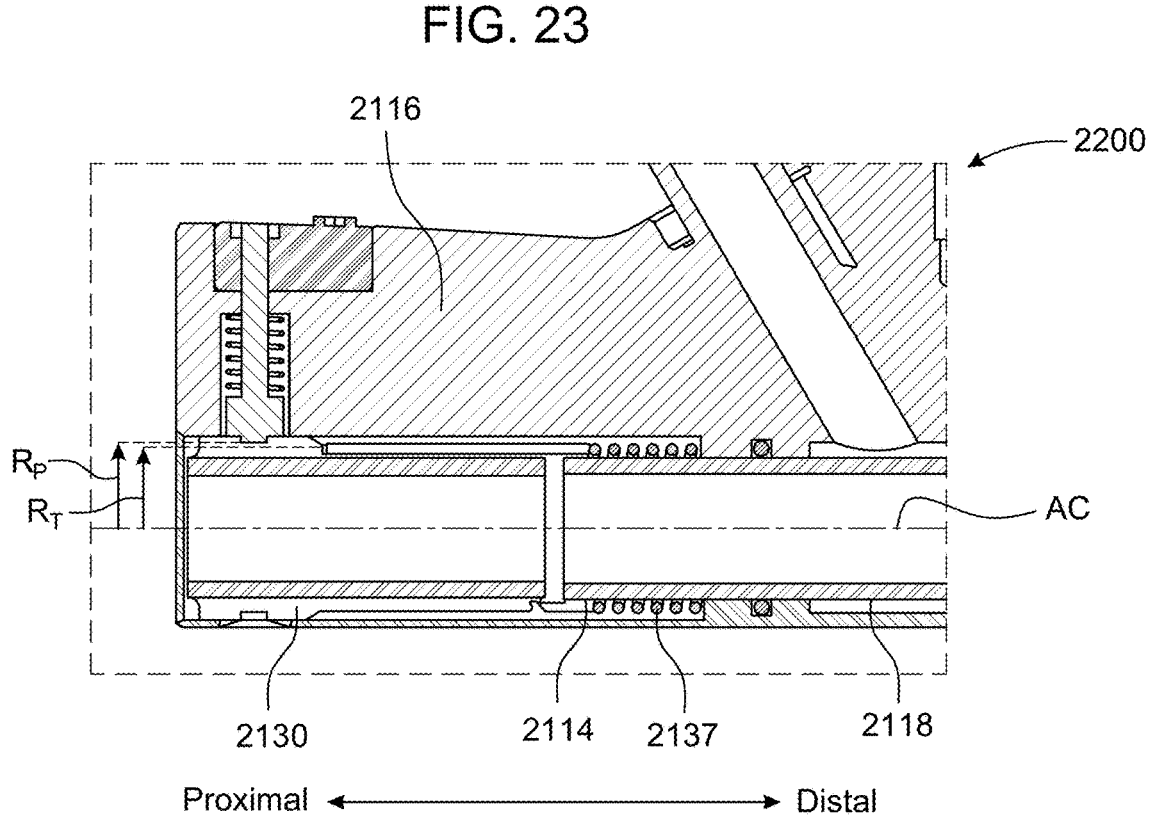
FIG. 24 is a side cross-sectional view of the cleaning device of FIG. 23.

The configurations and relative position of the retention pin 2344 and registration tab 2138 can be chosen to avoid interference between the retention pin 2344 and the lead-in shoulders 2132 and 2133. For example, the radial position of the retention pin 2344 and its associated circumferential groove 2136 can differ from the radial position of the registration tab 2138 and the lead-in shoulders 2132 and 2133. In the exemplary embodiment of FIGS. 21-25, the cleaning device 2200 can have stepped internal radii that create two regions each having differing radial distances from a longitudinal central axis of the cleaning device 2200. Such an arrangement is illustrated in FIG. 24, in which an interface between an engagement portion 2345 of the retention pin 2344 and the groove 2136 of the collar 2130 is positioned a radial distance $R_P$ from a longitudinal central axis $A_C$ of the cleaning device 2200. The registration tab 2138 and the lead-in shoulders 2132, 2133 are positioned a radial distance $R_T$ from the central axis $A_C$. The radial distance $R_P$ from the central axis $A_C$ is larger than the radial distance $R_T$ from the central axis $A_C$, and the difference in radial distance from the central axis prevents the retention pin 2344 from contacting the lead-in shoulders 2132 and 2133 as the cleaning device 2200 is installed over the shaft 2118 in a distal to proximal direction. This arrangement prevents undesirable contact (e.g., jamming) of the retention pin 2344 against the lead-in shoulders 2132 and 2133, because the retention pin is located radially outward from the lead-in shoulders 2132, 2133 relative to the central axis $A_C$.

As discussed above, in some embodiments, the distal end of the cleaning device must be fully seated against the distal end of the shaft of the imaging device for the cleaning device to function correctly. Manufacturing tolerances may lead to variations in the dimensions (e.g., length) of both the cleaning device and the imaging device shaft, and such variations may impact the relative positions of the distal ends of the imaging tool shaft and cleaning device in an installed position of the cleaning device. Accordingly, embodiments of the disclosure include features configured to account for longitudinal variations in length of the imaging device shaft to ensure that the distal end of the cleaning device seats fully on the distal end of the imaging device shaft in spite of such variations.

For example, some embodiments optionally include a biasing element configured to preload the distal end of the cleaning device against the distal end of the imaging device shaft while also absorbing any individual variations (e.g., due to manufacturing tolerances) from a nominal length of the imaging instrument shaft and/or the cleaning device. The cleaning device 2200 described in connection with FIGS. 21-25 includes a tubular member 2114 and a manifold portion 2116 rotatable relative to one another. The cleaning device 2200 optionally includes a preload device 2137, such as a coil spring or other biasing element, positioned between the tubular member 2114 and the manifold portion 2116. The preload device 2137 biases the manifold portion 2116 in a distal direction relative to the tubular member 2114. After the user inserts the shaft 2118 of the imaging instrument 2112 in the tubular member 2114 of the cleaning device, the manifold portion 2116 must be pushed in the proximal direction against the biasing force of the preload device 2137 for the retention pin 2344 to enter the groove 2136 of the collar 2130, thereby partially compressing the preload device 2137. Once the retention pin 2344 enters the circumferential groove 2136, the preload device 2137 is maintained in a partially compressed position and holds the distal end of the cleaning device in place against the distal end of the imaging instrument shaft. This arrangement ensures the cleaning device is fully seated on the imaging instrument shaft regardless of minor variations in length of the imaging instrument shaft and/or cleaning device. Further, once the retention pin 2344 enters the groove 2136 of the collar 2130, interaction between the retention pin 2344 and the groove 2136 resists further proximal movement of the cleaning device relative to the imaging instrument 2112, indicating the fully installed state to the user.

Figure 25:
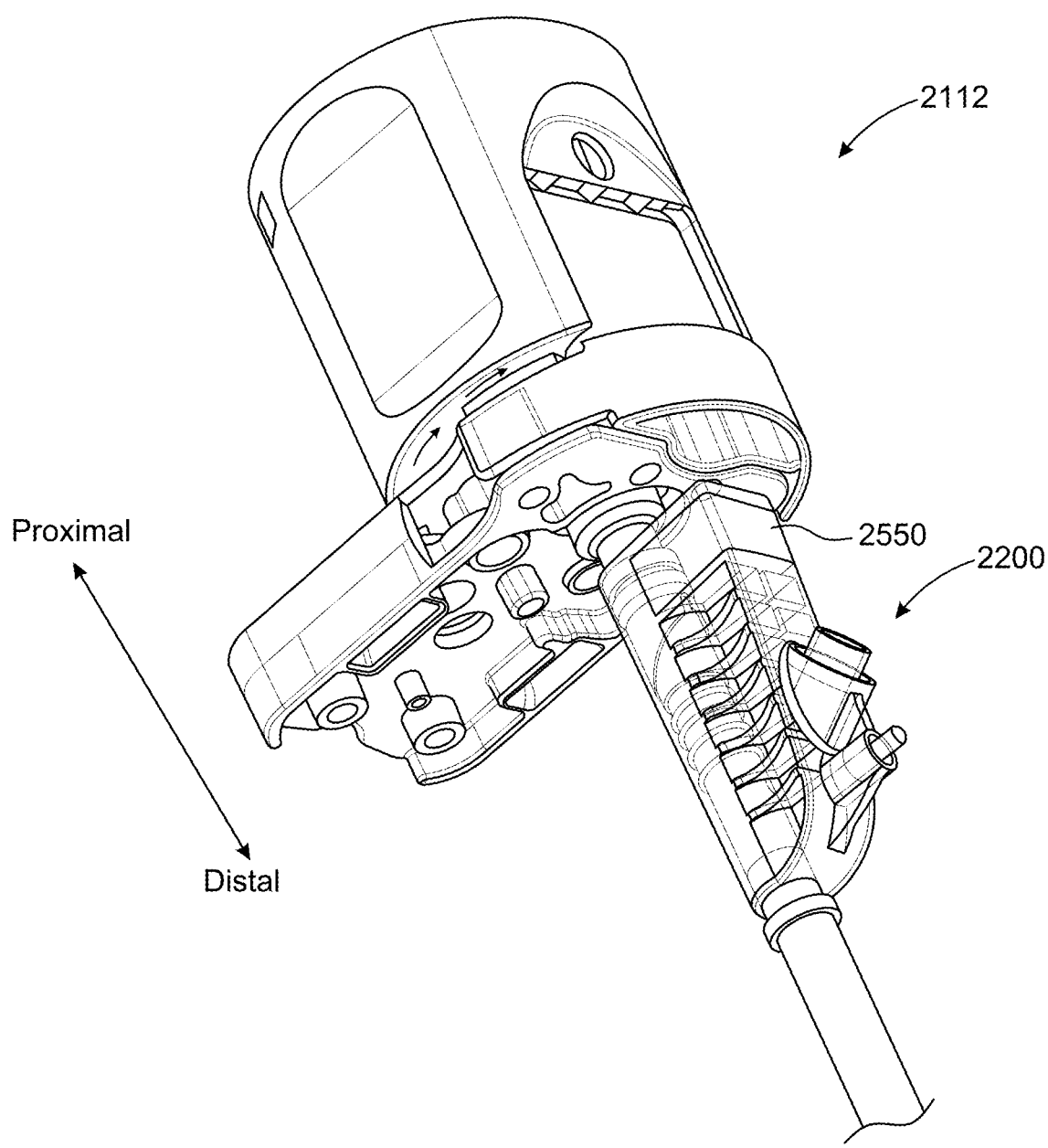
FIG. 25 is a perspective view of the imaging instrument and cleaning device according to FIG. 23.

FIG. 25 shows a partial, perspective view of the cleaning device 2200 fully installed on the proximal portion of the imaging device 2112. To remove the cleaning device 2200 from the imaging device 2112, a user pulls on release portion 2550, which optionally may be directly coupled to the retention pin 2344 (FIG. 23), to raise the retention pin 2344 from the circumferential groove 2136 (FIG. 23). While pulling on the release portion 2550, the user slides the cleaning device 2200 in a distal direction along the shaft 2118 until the retention pin 2344 clears the circumferential groove 2136, thereby releasing the cleaning device 2200 from the collar 2130 (FIG. 23) and imaging device shaft 2118 (FIG. 23).

Figure 26A:
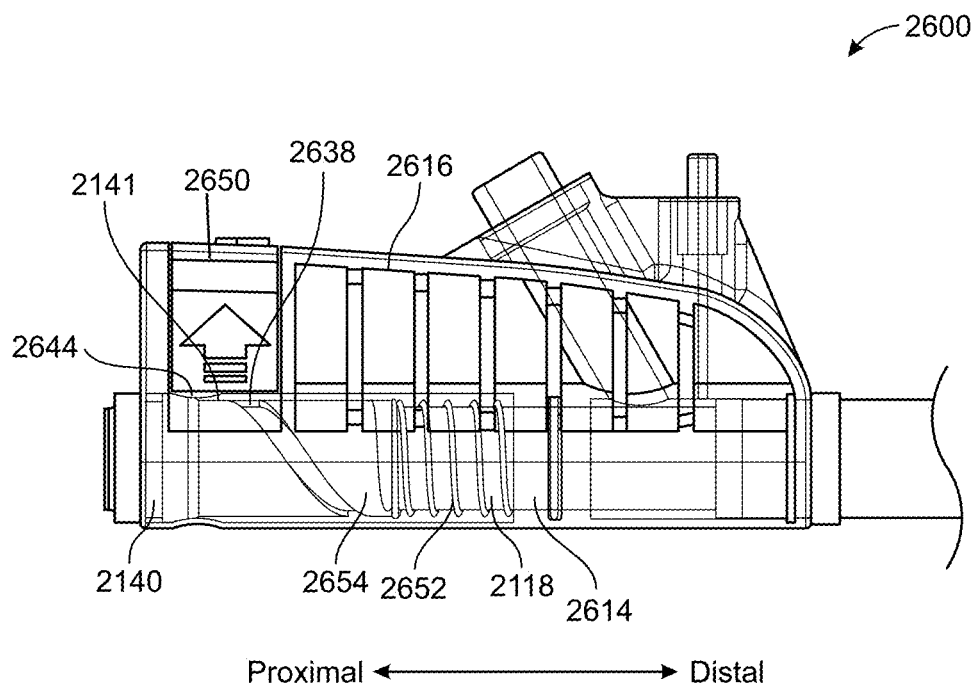
FIGS. 26A and 26B are side views of a cleaning device according to another exemplary embodiment of the present disclosure.
Figure 26B:
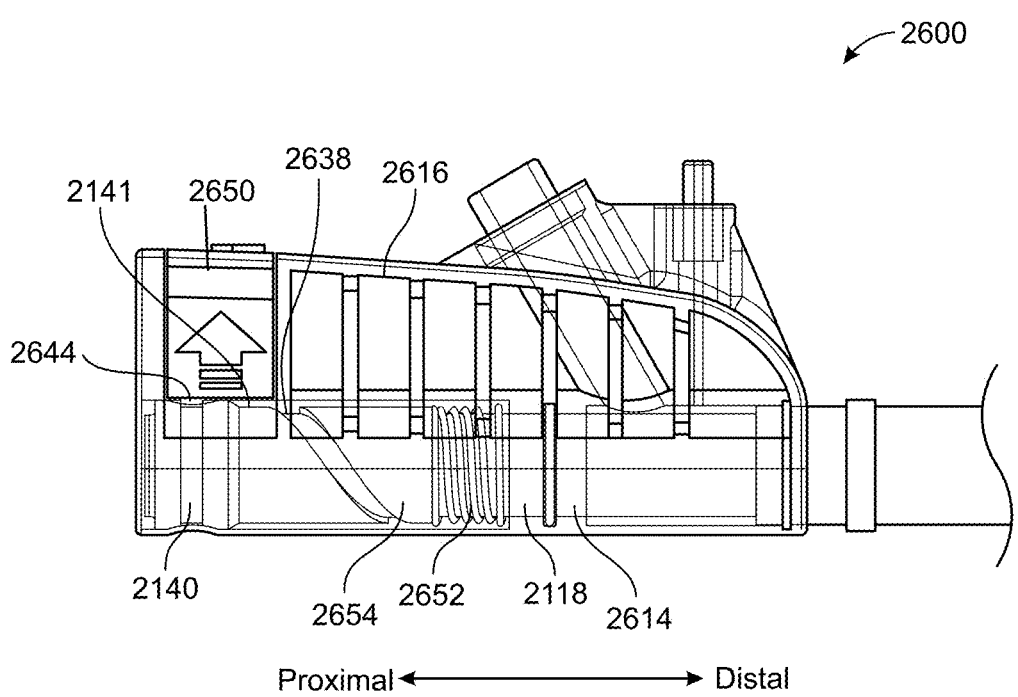

Cleaning devices according to the present disclosure optionally include one or more features that assist the user in removing the cleaning device from the imaging device 2112. For example, referring to FIGS. 26A and 26B, another exemplary embodiment of a cleaning device 2600 is shown. The imaging device 2112 (FIG. 25), shaft 2118, and collar 2130 are substantially as described above in connection with FIGS. 21-25. The cleaning device 2600 includes a preload device 2652, such as a spring or other biasing element. In the exemplary embodiment of FIGS. 26A and 26B, the preload device 2652 is a coil spring that surrounds the shaft 2118 of the imaging device 2112. The preload device 2652 is positioned between a tubular member 2614 of the cleaning device 2600 and a registration member 2654 that carries a registration tab 2638. The cleaning device 2600 includes a retention pin 2644 that is coupled to the tubular member 2614 by a manifold 2616. Thus, the registration member 2654 can move longitudinally relative to the tubular member 2614 and manifold 2616 when the preload device 2652 is extended or compressed.

To install the cleaning device 2600 on the shaft 2118, the user pushes the cleaning device 2600 over the shaft 2118 in a distal to proximal direction until the registration tab 2638 enters the recess 2141 of the collar 2130. As the cleaning device 2600 is pushed further over the shaft 2118 in a distal to proximal direction, the preload device 2652 is compressed, and the retention pin 2644 enters the circumferential groove 2136 to retain the cleaning device 2600 on the shaft 2118. In this installed state, shown in FIG. 26B, the preload device 2652 is partially compressed. Thus, when the user pulls radially outward on release portion 2650 (which is coupled to the retention pin 2644) to remove the cleaning device 2600 from the shaft 2118, the retention pin 2644 is removed from the circumferential groove 2136. On removal of the retention pin 2644 from the circumferential groove 2136, the preload device 2652 extends and automatically pushes cleaning device 2600 partially from the shaft 2118 in a proximal to distal direction. Thus, the cleaning device 2600 requires only a single movement of the user to be fully disengaged from the collar, i.e., a radially outward pull on the release portion 2650, after which the cleaning device 2600 can be removed from the shaft 2118 in a proximal to distal direction.

Figure 27A:
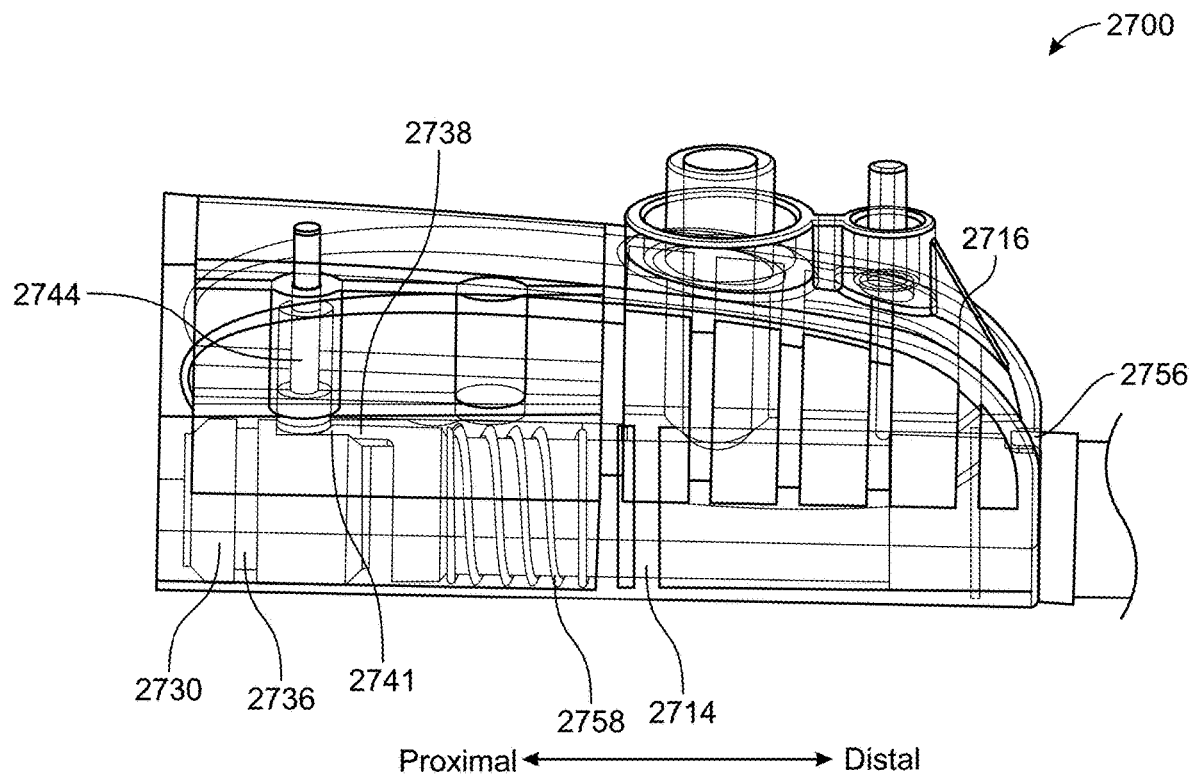
FIGS. 27A and 27B are side views of a cleaning device according to yet another exemplary embodiment of the present disclosure.
Figure 27B:
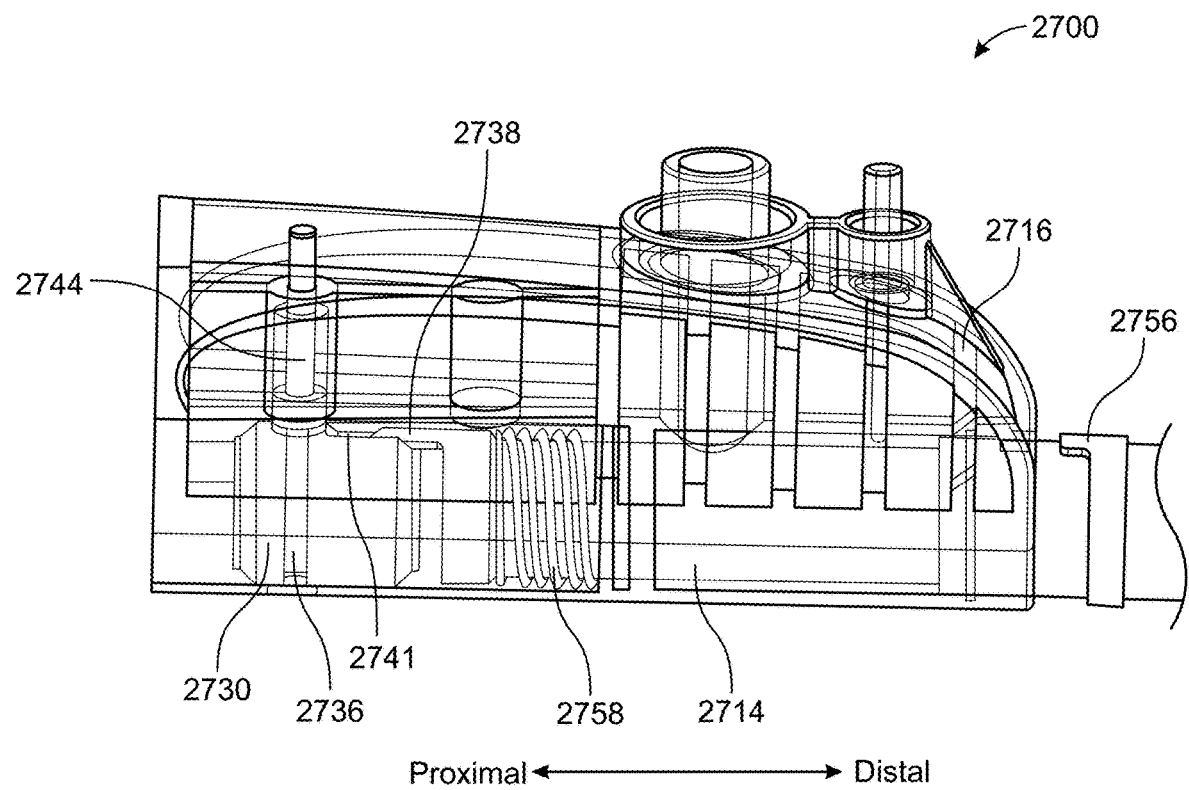

Referring now to FIGS. 27A and 27B, another exemplary embodiment of a cleaning device 2700 is shown. In this exemplary embodiment, the imaging device 2112 (FIG. 23) and shaft 2118 (FIG. 21) are substantially as described in connection with FIGS. 21-25. A collar 2730 includes a circumferential groove 2736 and a recess 2741. The collar 2730 does not include lead-in shoulders, because the exemplary embodiment of FIGS. 27A and 27B includes different features for ensuring correct rotational orientation between the cleaning device 2700 and the shaft 2118.

With continued reference to FIGS. 27A and 27B, the tubular member 2714 includes a collar registration tab 2738 and a manifold registration tab 2756. The tubular member 2714 extends through a portion of a manifold 2716, and the manifold 2716 is biased in a distal direction relative to the tubular member 2714 by a biasing device 2758. In the configuration shown in FIG. 27A, the manifold registration tab 2756 is engaged with the manifold 2716, and the tubular member 2714 and the manifold 2716 are not rotatable relative to one another. Thus, when a user is installing the cleaning device 2700 on an imaging instrument, the user can grip the manifold 2716 and rotate the manifold 2716 to a position in which the collar registration tab 2738 engages the recess 2741 of the collar 2730. Once the collar registration tab 2738 is engaged with the recess 2741, the manifold 2716 is pushed further proximally over the shaft 2118, compressing the biasing device 2758, until the retention pin 2744 enters the circumferential groove 2736, retaining the cleaning device 2700 over the shaft 2118 as shown in FIG. 27B. Compression of the biasing device 2758 also causes proximal movement of the manifold 2716 relative to the tubular member 2714, and the manifold registration tab 2756 disengages from the manifold 2716, thereby permitting rotational movement of the tubular member 2174 and shaft 2118 relative to the manifold 2716, as discussed elsewhere herein (e.g., FIG. 4 and the associated description). To remove the cleaning device 2700, the user pulls radially outward on release portion 2750, and as a result the retention pin is removed from the circumferential groove 2736, and the cleaning device 2700 can be removed as discussed in connection with FIGS. 26A and 26B above.

Coupling the manifold 2716 and tubular member 2714 such that relative rotation between the two is prevented during alignment and installation of the cleaning device 2700 makes the assembly easier to grasp and rotate into alignment during installation. In addition, during installation of the cleaning device 2700 such an arrangement reduces or eliminates any tangling or undue tension on fluid supply tubes or other components connected to the manifold 2716.

Figure 28A:
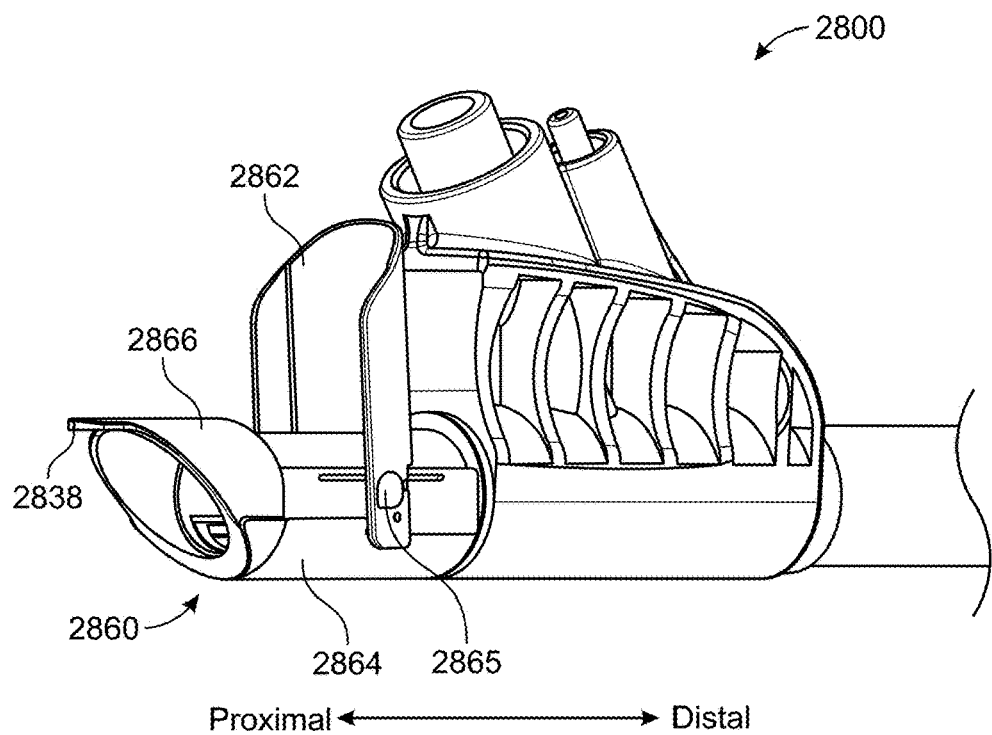
FIGS. 28A and 28B are perspective views of a cleaning device according to yet another exemplary embodiment of the present disclosure.
Figure 28B:
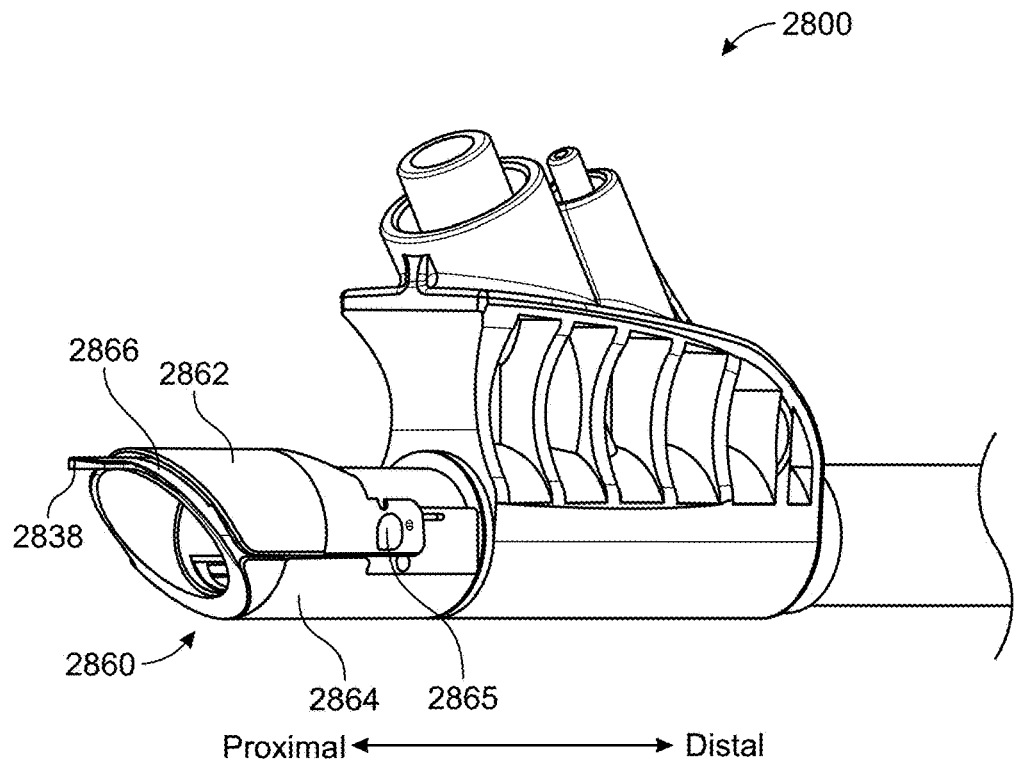

Referring now to FIGS. 28A and 28B, another cleaning device 2800 is shown. The cleaning device 2800 is configured to be coupled to an imaging device with a collar similar to the collar 2130 discussed in connection with FIGS. 21-24. The cleaning device 2800 includes a clamp 2860 forming a proximal end portion of the cleaning device 2800. The clamp 2860 includes a clamp lever 2862 and a movable member 2864. The clamp lever 2862 is pivotably coupled to a clamp body 2866. FIG. 28A shows the clamp 2860 in an open position, in which the cleaning device 2800 can be positioned over a shaft (e.g., shaft 2118 shown in FIG. 21). The clamp body 2866 includes a registration tab 2838 to facilitate rotational alignment of the cleaning device 2800 with the shaft 2118, e.g., by engaging the registration tab 2838 with a recess in a collar, as discussed in connection with FIGS. 21-25. Once the cleaning device 2800 is positioned over the shaft 2118 (FIG. 21) and aligned, the clamp lever 2862 is closed to the position shown in FIG. 28B. The clamp lever 2862 is optionally coupled to the movable member 2864 by a cam 2865 or other eccentric device, and upon closing the clamp lever 2862, the movable member 2864 is brought tightly against the shaft so that the shaft is gripped between the movable member 2864 and the clamp body 2866, thereby retaining the cleaning device 2800 on the shaft. Removal of the cleaning device 2800 from the shaft is accomplished by raising the clamp lever 2862, which releases the hold of the clamp body 2866 and movable member 2864 on the shaft, thus allowing removal of the cleaning device from the shaft.

Figure 29:
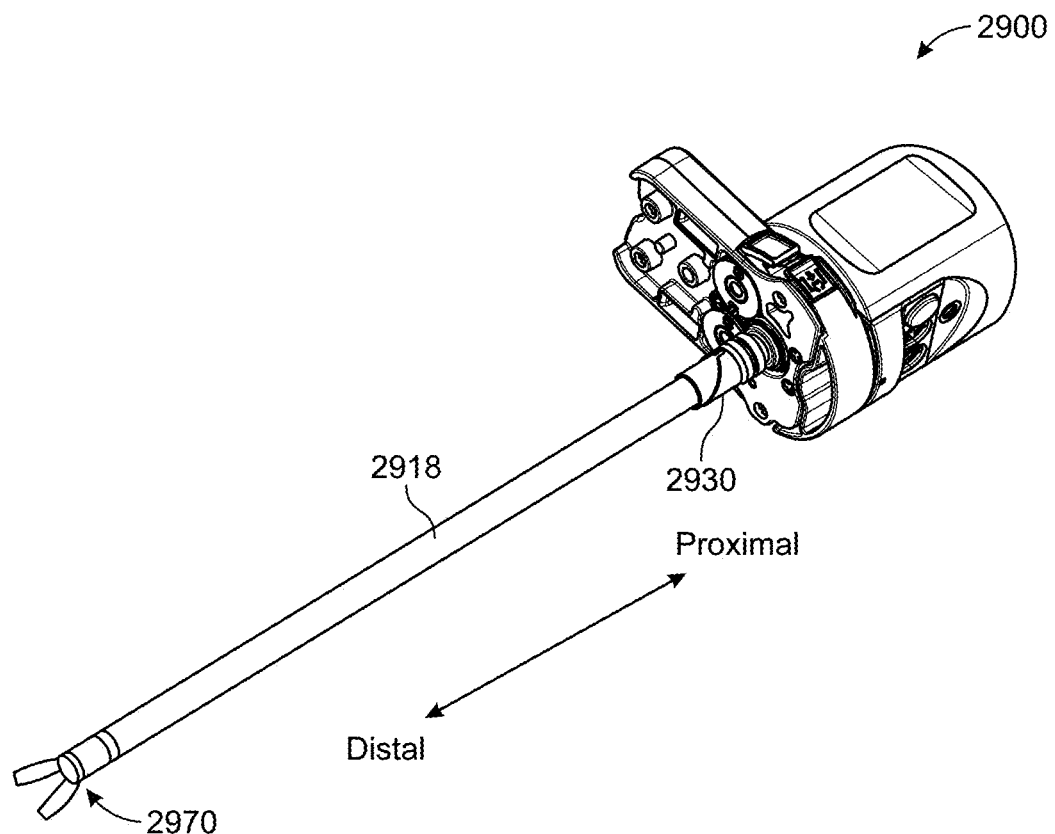
FIG. 29 is a schematic view of an instrument according to an exemplary embodiment of the present disclosure.

FIG. 29 shows a schematic view of an instrument 2900 comprising an end effector 2968 that can be or include end effectors other than imaging instruments as discussed elsewhere herein. In this exemplary embodiment, the end effector 2968 includes jaws 2970. Other instruments for which aspects of the present disclosure can have application include, without limitation, tools such as forceps, staplers, clip appliers, needle drivers, electrosurgical tools, or any other medical or non-medical tools. The instrument 2900 includes a shaft 2918 with an engagement portion, such as a collar 2930 attached to the shaft 2918 or integrated with the shaft 2918. The collar 2930 can be similar to the collar 2130 discussed in connection with FIG. 22 and can include lead-in shoulders and a recess like those discussed in connection with the collar 2130. The collar 2930 can be, without limitation, formed integrally with, permanently attached to, or removably attached to the shaft 2918.

Figure 30:
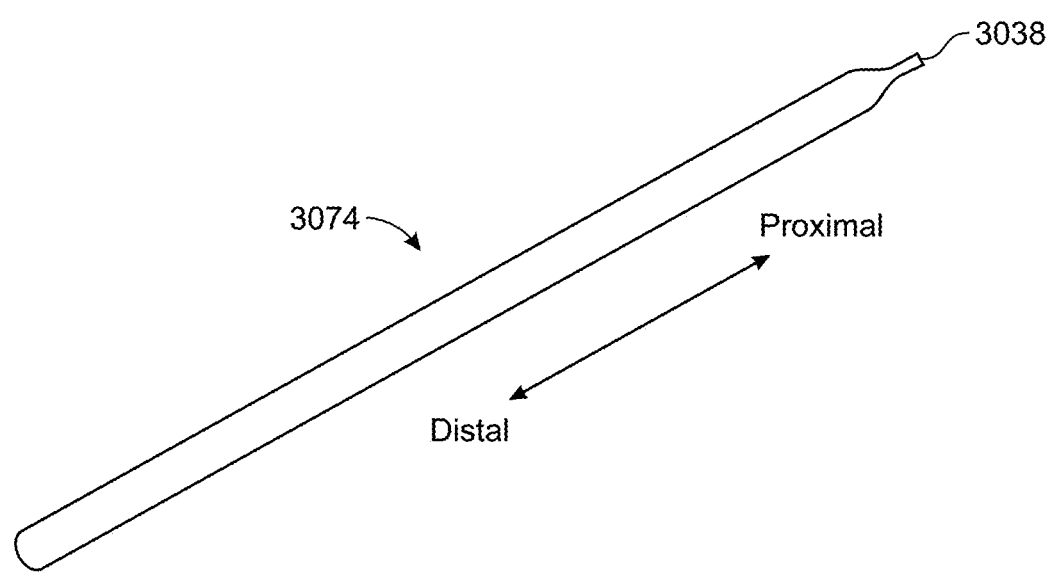
FIG. 30 is a schematic view of an instrument sheath according an exemplary embodiment of the present disclosure.

FIG. 30 shows a schematic view of an instrument sheath 3074 that can, without limitation, provide cleaning functionality similar to other embodiments discussed in the present disclosure, protection for articulatable joints or other components of the instrument 2900, or other functionality. The instrument sheath 3074 includes a registration tab 3038 that is configured to be received in a recess (not shown; similar to recess 2141 of collar 2130 shown in FIG. 22) of the collar 2930 in an installed position of the instrument sheath 3074 on the instrument 2900, thereby establishing a rotational orientation relationship between the instrument sheath 3074 and the instrument 2900. Interaction between the lead-in shoulders, the registration tab 3038, and the recess provides automatic alignment of the instrument sheath 3074 relative to the instrument 2900 in a similar manner to that discussed in connection with the embodiment of FIGS. 21-25.

Embodiments of the disclosure provide cleaning devices for imaging instruments that can be retrofitted to existing imaging instruments without significant modifications to the imaging instruments. Further, while the present disclosure includes collars configured to be installed on shafts of imaging instruments not originally equipped with cleaning devices, the disclosure is not so limited and imaging instruments having collars to retain a cleaning device and which are integrated with the shaft are within the scope of the disclosure, including any or all of the features of the non-integrated collar designs disclosed herein, such as collars 330, 830, 930, 1430, 1530, 1630, 1730, 1892, or combinations thereof. The disclosed devices enable in situ cleaning of an imaging instrument viewing portion while the imaging instrument viewing portion is located to capture images of a remote site of interest without the need to remove the imaging instrument to access the viewing portion. Such devices are configured to prevent obscuring a field of view of the imaging instrument, thereby providing consistent and reliable visualization of a remote site of interest. In addition, embodiments of the disclosure provide instrument sheaths or similar tubular members that include features configured to facilitate installation of the sheath in a predetermined rotational orientation relative to an instrument.

Embodiments incorporating inventive aspects described herein may be used, for example, with remotely operated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, embodiments incorporating one or more aspects described herein may be used, for example, with a da Vinci® Surgical System, such as the da Vinci Xi® Surgical System or the da Vinci X Surgical System, all commercialized by Intuitive Surgical, Inc., of Sunnyvale, California. Although various embodiments described herein are discussed with regard to imaging instruments used with a manipulating system of a teleoperated surgical system, the present disclosure is not limited to use with imaging instruments for a teleoperated surgical system. Various embodiments described herein can optionally be used in conjunction with hand-held, manual imaging instruments, or other imaging instruments that are configured to provide images of remote sites to assist in performing procedures remotely at such remote sites. For example, various space exploration and other remote inspection and/or sensing applications are considered within the scope of the present disclosure.

As discussed above, in accordance with various embodiments, devices of the present disclosure are configured for use in teleoperated, computer-assisted surgical systems (sometimes referred to as robotic surgical systems). Referring now to FIG. 19, an embodiment of a manipulating system 1900 of a teleoperated, computer-assisted surgical system, to which surgical instruments are configured to be mounted for use, is shown. Such a surgical system may further include a surgeon console (not shown) for receiving input from a user to control instruments of manipulating system 1900, as well as an auxiliary system, such as a control/vision cart (not shown), as described in, for example, U.S. Pat. Nos. 9,358,074 and 9,295,524, incorporated above. As those having ordinary skill in the art would appreciate, either or both of the surgeon console and the auxiliary system can include a display for displaying the images obtained from the imaging instrument.

As shown in the embodiment of FIG. 19, manipulating system 1900 includes a base 1020, a main column 1040, and a main boom 1060 connected to main column 1040. Manipulating system 1900 also includes a plurality of arms 1100, 1110, 1120, 1130, which are each connected to main boom 1060. Arms 1100, 1110, 1120, 1130 each include an instrument mount portion 1200 to which an instrument 1300 may be mounted, which is illustrated as being attached to arm 1100. Portions of arms 1100, 1110, 1120, 1130 may be manipulated during a surgical procedure according to commands provided by a user at the surgeon console. In an embodiment, signal(s) or input(s) transmitted from a user control system are transmitted to the auxiliary system, which may interpret the input(s) and generate command(s) or output(s) to be transmitted to the manipulating system 1900 to cause manipulation of an instrument 1300 (only one such instrument being mounted in FIG. 19) and/or portions of arm 1100 to which the instrument 1300 is coupled at the manipulating system 1900.

Instrument mount portion 1200 comprises a drive assembly 1220 and a cannula mount 1240, with an instrument carriage 1340 of the instrument 1300 connecting with the drive assembly 1220, according to an embodiment. Cannula mount 1240 is configured to hold a cannula 1360 through which a shaft 1320 of instrument 1300 may extend to a surgery site during a surgical procedure. Drive assembly 1220 contains a variety of drive and other mechanisms that are controlled to respond to input commands at the surgeon console and transmit forces to the instrument carriage 1340 to actuate the instrument 1300, as those skilled in the art are familiar with.

Although the embodiment of FIG. 19 shows an instrument 1300 attached to only arm 1100 for ease of viewing, an instrument may be attached to any and each of arms 1100, 1110, 1120, 1130. An instrument 1300 may be a surgical instrument with an end effector as discussed herein. A surgical instrument with an end effector may be attached to and used with any of arms 1100, 1110, 1120, 1130. The embodiments described herein are not limited to the embodiment of FIG. 19, and various other teleoperated, computer-assisted surgical system configurations may be used with the embodiments described herein.

Other configurations of surgical systems, such as surgical systems configured for single-port surgery, are also contemplated. For example, with reference now to FIG. 20, a portion of an embodiment of a manipulator arm 2140 of a manipulating system with two surgical instruments 2300, 2310 in an installed position is shown. The schematic illustration of FIG. 20 depicts only two surgical instruments for simplicity, but more than two surgical instruments may be received in an installed position at a manipulating system as those having ordinary skill in the art are familiar with. Each surgical instrument 2300, 2310 includes an instrument shaft 2320, 2330 that at a distal end has a moveable end effector or, if the instrument is an imaging instrument, an endoscope, camera, or other sensing device, and may or may not include a wrist mechanism (not shown) to control the movement of the distal end.

In the embodiment of FIG. 20, the distal end portions of the instruments 2300, 2310 are received through a single port structure 2380 to be introduced into the patient. Other configurations of manipulating systems that can be used in conjunction with the present disclosure can use several individual manipulator arms. In addition, individual manipulator arms may include a single instrument or a plurality of instruments. Further, an instrument may be a surgical instrument with an end effector or may be a sensing instrument utilized during a surgical procedure to provide information, (e.g., visualization, electrophysiological activity, pressure, fluid flow, and/or other sensed data) of a remote site. Thus, one or more of the instruments may be an imaging instrument in accordance with various embodiments of the present disclosure.

The systems of FIGS. 19 and 20 also may include an operably coupled display device, generally labeled as 1500, 2500. The display device 1500, 2500 can include one or more displays that are part of the user control interface (now shown), and/or the auxiliary cart (not shown), and/or as a stand-alone component. The display device 1500, 2500 may be operably coupled to receive image data from an imaging instrument operably coupled to one of the manipulator arms 1100, 1110, 1120, 1130, 2420, 2430 to display images of the remote site, for example, real-time images, as those having ordinary skill in the art are familiar. The display device 1500, 2500 also may be operably coupled to the control system of the teleoperated system and be configured to display various graphical user interface images that can be controlled based on system use parameters and to provide additional information regarding system status to a user.

This description and the accompanying drawings that illustrate various embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A system, comprising:
   an imaging instrument, comprising:
      a shaft comprising a proximal end portion and a distal end portion,
      a lens at the distal end portion of the shaft, and
      a collar at the proximal end portion of the shaft,
      wherein, in a first state, a position of the collar relative to the shaft is adjustable by rotation and axial movement,
      wherein, in an installed state of the collar relative to the shaft, an interior surface of the collar engages with the shaft and fixes the collar rotatably and axially relative to the shaft, and
      wherein a position of the collar relative to the shaft in the installed state is adjustable by one or both of rotation and axial movement of the collar relative to the shaft while the collar is in the first state; and
   a cleaning device coupled to the imaging instrument, the cleaning device comprising:
      a tubular member sized to receive the shaft of the imaging instrument, and
      a latching element coupled to the tubular member and configured to couple to the collar to retain the tubular member on the shaft of the imaging instrument and to maintain a relative rotational relationship between the tubular member and the shaft of the imaging instrument.

2. The system of claim 1, wherein:
   the collar comprises a collet and a retaining sleeve configured to couple with the collet.

3. The system of claim 2, wherein:
   the collet comprises grip features configured to grip the shaft on the condition the retaining sleeve is coupled with the collet.

4. The system of claim 3, wherein:
   the grip features comprise longitudinal portions separated by longitudinal reliefs.

5. The system of claim 4, wherein:
   the collet comprises external threading; and
   the retaining sleeve comprises internal threading configured to engage with the external threading of the retaining sleeve.

6. The system of claim 3, wherein:
   the grip features comprise one or more resilient material portions forming an interior surface of the collet.

7. The system of claim 2, wherein:
   the collet comprises one or more recesses; and
   the retaining sleeve comprises one or more engagement members configured to engage the one or more recesses.

8. The system of claim 1, wherein:
   the latching element comprises a flange; and
   the collar comprises a groove in which the flange is received on the condition the cleaning device is coupled with the imaging instrument.

9. The system of claim 8, wherein:
   the latching element is flexibly coupled to the cleaning device by a resilient portion.

10. The system of claim 8, wherein:
    the latching element comprises a tab operable by a user to disengage the flange of the latching element from the groove of the collar.

11. The system of claim 1, wherein:
    the latching element comprises a spring clip; and
    the collar comprises a groove into which the spring clip is received on the condition the cleaning device is coupled with the imaging instrument.

12. The system of claim 1, wherein:
    the latching element comprises one or more barbs;
    the collar comprises one or more complementary barbs; and
    engagement between the one or more barbs and the one or more complementary barbs retains the cleaning device on the imaging instrument.

13. The system of claim 1, wherein:
    the shaft comprises at least one dimple;
    the collar comprises at least one protrusion; and
    the at least one protrusion is positioned in the at least one dimple.

14. The system of claim 1, wherein:
    the collar comprises a plurality of longitudinal ridges on an interior surface of the collar.

15. The system of claim 1, wherein:
    the collar is diametrically split in two halves; and
    the collar further comprises a retainer configured to retain the two halves on the shaft.

16. The system of claim 1, wherein:
    the collar comprises an outer diameter, a lead-in shoulder extending at least partially around the outer diameter of the collar, and a recess;
    the lead-in shoulder comprises a proximal end, and the recess of the collar is at the proximal end of the lead-in shoulder; and
    the latching element comprises a registration tab configured to be received in the recess of the collar.

17. The system of claim 16, wherein:
    the lead-in shoulder is a first lead-in shoulder;
    the collar further comprises a second lead-in shoulder; and
    the first lead-in shoulder and the second lead-in shoulder extend in opposite directions at least partially around the outer diameter of the collar.

18. The system of claim 17, wherein:
    the first lead-in shoulder and the second lead-in shoulder meet at a distal base area and at a proximal apex area.

19. The system of claim 1, wherein:
    the collar comprises a circumferential groove; and
    the latching element comprises a retention pin biased to enter the circumferential groove in an installed state of the tubular member on the collar.

20. The system of claim 1, wherein:
the latching element further comprises a biasing element that biases the tubular member in a proximal direction relative to the collar along a longitudinal axis of the tubular member.

21. The system of claim 1, wherein:
a longitudinal axis of the tubular member is defined;
the cleaning device comprises a manifold, a biasing element, a manifold registration tab, and a tubular member registration tab;
the manifold is rotatably coupled to the tubular member;
the biasing element biases the manifold in a distal direction along the longitudinal axis of the tubular member;
the manifold registration tab is configured to rotationally lock the manifold with the tubular member in an extended state of the biasing element;
the tubular member registration tab is configured to engage the collar; and
in an installed position of the cleaning device on the imaging instrument, the biasing element is in a compressed state, and the manifold registration tab is disengaged from the manifold.

22. The system of claim 1, wherein:
the latching element comprises a clamping device configured to engage the shaft of the imaging instrument to retain the cleaning device on the imaging instrument.

* * * * *